(12) United States Patent
Medvedev et al.

(10) Patent No.: US 12,708,890 B2
(45) Date of Patent: Aug. 18, 2026

(54) PLASMA REACTOR AND PLASMA CHEMICAL REACTIONS

(71) Applicant: NANOPLAZZ TECHNOLOGIES LTD., Tirat Hacarmel (IL)

(72) Inventors: Dmitry Medvedev, Moscow (RU); Mikhail Marin, Moscow (RU); Evgeny Gorelik, Khimki (RU); Boris Mislavsky, Moscow (RU); Roman Iliev, Moscow (RU)

(73) Assignee: NANOPLAZZ TECHNOLOGIES LTD., Tirat Hacarmel (IL)

( * ) Notice: Subject to any disclaimer, the term of this patent is extended or adjusted under 35 U.S.C. 154(b) by 649 days.

(21) Appl. No.: 18/020,002

(22) PCT Filed: Aug. 4, 2021

(86) PCT No.: PCT/IB2021/057174
§ 371 (c)(1),
(2) Date: Feb. 6, 2023

(87) PCT Pub. No.: WO2022/029663
PCT Pub. Date: Feb. 10, 2022

(65) Prior Publication Data

US 2023/0285927 A1 Sep. 14, 2023

Related U.S. Application Data

(60) Provisional application No. 63/061,939, filed on Aug. 6, 2020.

(51) Int. Cl.
*B01J 19/08* (2006.01)
*C01B 3/047* (2026.01)
(Continued)

(52) U.S. Cl.
CPC ............ *B01J 19/088* (2013.01); *C01B 3/047* (2013.01); *C01B 3/24* (2013.01); *C01B 3/342* (2013.01);
(Continued)

(58) Field of Classification Search
CPC ............. B01J 19/088; B01J 2219/0809; B01J 2219/083; B01J 2219/0869; B01J 2219/0875; B01J 2219/0896
See application file for complete search history.

(56) References Cited

U.S. PATENT DOCUMENTS 8,603,403 B2 12/2013 Gutsol
10,477,666 B2 11/2019 Medvedev
(Continued)

FOREIGN PATENT DOCUMENTS

CN 111362278 A 7/2020
JP 2005139052 A 6/2005
(Continued)

OTHER PUBLICATIONS

Zhu, F., Zhang, H., Li, X., Wu, A., Yan, J., Ni, M., & Tu, X. (2018). Arc dynamics of a pulsed DC nitrogen rotating gliding arc discharge. Journal of Physics D: Applied Physics, 51(10), 105202. doi:10.1088/1361-6463/aaa9eb.
(Continued)

*Primary Examiner* — Lessanework Seifu
(74) *Attorney, Agent, or Firm* — The Roy Gross Law Firm, LLC; Roy D. Gross

(57) ABSTRACT

The present disclosure is related to the field of chemistry and provides methods and devices for stimulation of endothermic reactions in gas phase with high activation barriers by nanosecond pulsed electrical discharge. It can be used for, e.g., $CO_2$ functionalization of methane, $H_2S$ dissociation, hydrogen and syngas production, for processing ammonia
(Continued)

synthesis and dissociation, etc. Some embodiments include methods and devices associated with the stimulation of plasma chemical reactions with nanosecond pulse electric discharge in the presence of gas flow.

8 Claims, 19 Drawing Sheets

(51) Int. Cl.

| | |
|---|---|
| ***C01B 3/24*** | (2006.01) |
| ***C01B 3/34*** | (2006.01) |
| ***C01B 17/04*** | (2006.01) |
| ***C01B 32/40*** | (2017.01) |
| ***C01C 1/04*** | (2006.01) |
| ***C07C 2/80*** | (2006.01) |
| ***H02M 7/5387*** | (2007.01) |
| ***H05H 1/24*** | (2006.01) |

(52) U.S. Cl.

CPC .......... *C01B 17/0495* (2013.01); *C01B 32/40* (2017.08); *C01C 1/0494* (2013.01); *C07C 2/80* (2013.01); *H02M 7/5387* (2013.01); *H05H 1/24* (2013.01); *B01J 2219/0809* (2013.01); *B01J 2219/083* (2013.01); *B01J 2219/0869* (2013.01); *B01J 2219/0875* (2013.01); *B01J 2219/0896* (2013.01); *C01B 2203/0222* (2013.01); *C01B 2203/0272* (2013.01); *C01B 2203/1241* (2013.01); *H05H 2242/22* (2021.05); *H05H 2245/10* (2021.05)

(56) References Cited

U.S. PATENT DOCUMENTS

| | | | | |
|---|---|---|---|---|
| 10,978,955 | B2 | 4/2021 | Ziemba | |
| 11,535,532 | B1 * | 12/2022 | Medvedev ........ | H01J 37/32348 |
| 2012/0090985 | A1 | 4/2012 | Rabinovich et al. | |
| 2012/0321527 | A1 | 12/2012 | Gutsol et al. | |

FOREIGN PATENT DOCUMENTS

| | | | |
|---|---|---|---|
| JP | 2007524963 | A | 8/2007 |
| JP | 2016007551 | A | 1/2016 |
| RU | 2687422 | C1 | 5/2019 |
| WO | 2018020434 | A1 | 2/2018 |
| WO | 2018081060 | A1 | 5/2018 |
| WO | 2020076186 | A1 | 4/2020 |

OTHER PUBLICATIONS

A Ozkan, Thierry Dufour, T Silva, N Britun, R Snyders, et al.. DBD in burst mode: solution for more efficient CO2 conversion?. Plasma Sources Science and Technology, 2016, 25 (5), pp. 055005. DOI: 10.1088/0963-0252/25/5/055005. published at https://hal.sorbonne-universite.fr/hal-01367345.

Bak, M. S., Im, S.-K., & Cappelli, M. (2015). Nanosecond-pulsed discharge plasma splitting of carbon dioxide. IEEE Transactions on Plasma Science, 43(4), 1002-1007. doi:10.1109/tps.2015.2408344.

Wu, A., Li, X., Yan, J., Yang, J., Du, C., Zhu, F., & Qian, J. (2017). Co-generation of hydrogen and carbon aerosol from coalbed methane surrogate using rotating gliding arc plasma. Applied Energy, 195, 67-79. DOI: 10.1016/j.apenergy.2017.03.043.

PCT International Search Report for International Application No. PCT/IB2021/057174, mailed Nov. 10, 2021, 4pp.

PCT Written Opinion for International Application No. PCT/IB2021/057174, mailed mailed Nov. 10, 2021, 6pp.

PCT International Preliminary Report on Patentability for International Application No. PCT/IB2021/057174, issued Feb. 7, 2023, 7pp.

* cited by examiner

PLASMA REACTOR AND PLASMA CHEMICAL REACTIONS

CROSS REFERENCES TO RELATED APPLICATIONS

This application is a National Phase of PCT Patent Application No. PCT/IB2021/057174 having International filing date of Aug. 4, 2021, which claims the benefit of priority of U.S. Provisional Patent Application No. 63/061, 939, filed on Aug. 6, 2020; the contents of which are all incorporated herein by reference in their entirety.

TECHNICAL FIELD

The present disclosure is related to the field of chemistry and provides methods and devices for stimulation of endothermic reactions in gas phase with high activation barriers by nanosecond pulsed electrical discharge. It can be used for, e.g., $CO_2$ functionalization of methane, $H_2S$ dissociation, hydrogen and syngas production, for processing ammonia synthesis and dissociation, etc. Some embodiments include methods and devices associated with the stimulation of plasma chemical reactions with nanosecond pulse electric discharge in the presence of gas flow.

BACKGROUND

Plasma can be regarded as a powerful tool for facilitating chemical reactions with a high activation energy, for example, in the production of synthetic natural gas, conversion of $CO_2$ and $H_2S$, etc. Plasma-based technologies can utilize barrier and pulsed discharges, electric arc, or a microwave discharge to produce plasma-chemical reactions that create a nonequilibrium plasma. Nonequilibrium plasma owes its name to the fact that the gas molecules may remain relatively cold (their temperature may not increase or may not increase significantly), while the electrons in the plasma have high enough energy to disassociate and ionize molecules.

Plasma parameters for production of a plasma-chemical reaction may be selected to reduce energy expenditure while increasing the yield of desired products. To stimulate direct chemical reactions, the plasma disassociates or excites the molecules of the reagents, producing radicals or other active particles, which can react with each other to achieve the desired products.

Various techniques for producing such reactions are described herein.

In a first case, source molecules may be disassociated by colliding them directly with electrons that have sufficient energy. In this case, an important characteristic of the plasma is the voltage of the electric field, and more specifically, the ratio of the electric field voltage to the concentration of the gas. This ratio determines whether the energy acquired by the electron in the electric field between collisions with gas molecules is enough for the desired process of forming radicals or active particles.

Such a technique may be used to produce nonequilibrium plasma, for example via barrier discharge, including intermittent barrier discharge described in the article, "DBD in burst mode: solution for more efficient CO2 conversion," A. Oskan et al (see Plasma Sources Science and Technology, IOP Publishing, 2016, 25 (5), p. 055005), published at https://hal.sorbonne-universite.fr/hal-01367345.

This technique may also apply to pulsed discharge as described, for example, in the article, "Nanosecond-Pulsed Discharge Plasma Splitting of Carbon Dioxide," Moon Soo Bak et al, (see IEEE TRANSACTIONS ON PLASMA SCIENCE, VOL. 43, NO. 4, APRIL 2015, pp. 1002-1007).

The described barrier discharge and pulsed discharge techniques, however, can suffer from low conversion process efficiency.

One problem of nonequilibrium plasma is that all types of energy loss experienced by the electrons (including collisions, vibrational excitation of molecules, etc.) that lead to heating of the gas are irreversible. Unfortunately, these types of losses are usually far greater than the molecule disassociation energy and even more so than the heat effect (enthalpy) of the reaction. For this reason, the energy efficiency of nonequilibrium plasma (the share of the heat effect in total energy losses of the process) is usually low—about 10%-20%.

An alternative is to heat up the gas molecules in a special reaction chamber to a temperature that is sufficient for them to break through the activation barrier of the reaction. In this case, the heating up is a useful process, and any processes resulting in more heat generation are not losses.

However, there is another problem when the reaction chamber is heated: all the molecules are heated, and the energy is spent not only on the heating and dissociation of the reagents that we need but also for heating and dissociating the final products of the reaction. In this case, a significant problem results from the reverse reactions that reduce the conversion rate and the energy efficiency of the process.

One solution for addressing this issue is to remove the reaction products from the hot area after their formation (e.g., in some cases, as soon as possible after formation). Due to this method of suppressing the reverse reactions, the yield of the desired products and the energy efficiency of the plasma-chemical processes can be increased. This approach may be referred to as the quenching of products of the plasma-chemical reactions.

A technology for conducting plasma-chemical reactions is described in US patent publication 2012/0090985 A1 published on Apr. 19, 2012. It involves a special plasma-chemical reactor that uses a gliding arc that moves through a gas flow organized as a reverse vortex. A geometry of gliding arc discharge is shown in FIG. 1. Plasma arc filaments created after first breakdown start moving and stretching by gas flow and arc stretching and cause an increase of working voltage and power of reactor. Here, (100) is a plasma-chemical reactor, **100*a* is a ground electrode, 100*b* is a high voltage electrode, 101 depicts a point of total extinction, 102 depicts a point of developed gliding arc when maximum energy is transferred, 103 depicts a point of gliding arc ignition, 104 depicts a DC power supply, 105 depicts a gas inlet, 106 depicts a reactor, and 107** depicts a plasma filament stretching by gas flow.

After applying a voltage to the electrodes, the electric breakdown takes place in the narrowest gap. Then the electric arc appearing after breakdown starts moving in the gas flow from the point with narrowest gap, so that the arc filament elongates. The voltage applied to this arc filament increases because of the increase of the filament length. At a moment when this voltage becomes sufficient for a new breakdown at the point with narrowest gap, the secondary breakdown takes place, and the process continues again and again. This repetitive mode is characteristic of different types of gliding arcs, such as rotating gliding arc, see Angjian Wu, Xiaodong Li, Jianhua Yan, Jian Yang, Changming Du, Fengsen Zhu, Jinyuan Qian, Co-generation of hydrogen and carbon aerosol from coalbed methane surrogate using rotating gliding arc plasma (Applied Energy, Vol. 195, 1 Jun. 2017, pp 67-79). Voltage and current waveforms of rotating gliding arc is shown on FIG. 2. It should be noted that the rotating gliding arc can also function in a stationary arc length mode.

Gliding arc plasma reactors can partially solve the problem of quenching the products by having them move through the plasma channel, but this solution also has some drawbacks stemming from the fact that the velocity of the plasma channel relative to the gas (the slippage velocity) is relatively low, at about 1 meter per second. Therefore, at least some of the reaction products manage to undergo secondary treatment, which leads to a significant contribution of reverse reactions and lowers the conversion rate and the energy efficiency of the process.

There is a need for systems that, on one hand, provide suitable gas conversion conditions in the hot zone while, at the same time, offer effective quenching of the reaction products. Such systems may significantly increase conversion and energy efficiencies. One such system is described in PCT/RU2019/000696. One goal of the described system is to increase efficiency of the process of converting gas/gas mixture into desired products by stimulating forward reactions and minimizing reverse reactions.

To achieve this effect, a plasma-chemical gas/gas mixture conversion process that involves creating a pulsed electrical discharge in the flow of the gas/gas mixture moving in the reaction chamber at a given velocity, which creates a plasma channel connecting the electrodes located inside the reaction chamber, is disclosed.

The disclosed method reduces quenching of reaction products generated in the hot plasma channel. The gas/gas mixture flow moving at a given velocity in the reaction chamber supplies new portions of reagents for the conversion while also helping to quickly extinguish the plasma channel that has just formed, thereby limiting its duration.

The high-voltage power supply unit creates a pulsed electrical discharge between the electrodes in the form of a hot plasma channel lasting between about 10-500 ns and with a frequency of between about 20-300 kHz.

This solution is quite efficient, but further improvements are still needed. For example, the systems and techniques described herein, which can address this need, also offer various improvements from the point of view of energy efficiency including energy efficiency of energy transfer from power supply to plasma, electrode lifetime, and system scalability, among others. These problems can be addressed, for example, by improvements in the reactor design and by controlling aspects of the gas flow velocity and directional control inside the reactor.

SUMMARY OF INVENTION

Disclosed are methods and apparatus aimed at stabilizing pulse electric discharge in gas flow, increasing energy efficiency including of efficiency of energy transfer from power supply to plasma, and for the scalability of plasma-chemical reactors. Controlling plasma parameters by controlling gas flow velocity and direction inside the reactor offers several significant challenges. By contrast with gliding arc discharge where a plasma filament is stretched by gas flow to increase voltage and decrease current, in nanosecond pulse discharge systems, gas flow will have little to no influence on the plasma filaments because the plasma filaments exist for only about 100 ns and there are no plasma filaments during the time between pulses (FIG. 2, FIG. 3). In FIG. 2, 201 corresponds to a continuously existing plasma filament stretched by gas flow, 202 corresponds to a moment when an old plasma filament is extinguishing and creating a new one, 203 corresponds to breakdown points, 204 corresponds to new arcs, 205 corresponds to elongation. In FIG. 3, 301 corresponds to a time no plasma exists. A plasma filament exists only during nanosecond breakdown times such as 302. Displacement of gas molecules during this time by gas flow velocity may be neglectable. In this case, one solution is to move the hot and excited gas trace after extinguishing the plasma filament rather than moving the plasma filament itself. Next breakdown locations in nanosecond hot plasma electric discharge are determined (or at least influenced) by residual traces of hot and excited gases remaining after a previous pulse. By moving such traces, the location of subsequent breakdown locations may be controlled (FIG. 4). FIG. 4 shows a portion of a plasma reaction system. This system includes an anode 401 and a cathode 402. In the described systems, gas may be flowed along a direction 403 as an axial gas flow, and a first break down 404 may occur which may result in a hot and excited gas trace 405. In the described systems, gas may be flowed along a direction 406 as a tangential gas flow. The a hot and excited gas trace (405, 407, 409) may migrate under the influence of the tangential gas flow (406, 408, 410), and a second breakdown in a new place may occur 411.

If a discharge gap will be different in different places, breakdown voltage can be controlled by moving a previous pulse trace in a direction of a location of a longer gap (FIG. 5). FIG. 5 shows a portion of a plasma reaction system. This system includes an anode (501) and a cathode (502). In the described systems, gas may be flowed along a direction 503 as an axial gas flow, and a first break down 504 may occur which may result in a hot and excited gas trace 505. In the described systems, gas may be flowed along a direction 506 as a tangential gas flow. The a hot and excited gas trace (505, 507, 509) may migrate under the influence of the tangential gas flow (506, 508, 510), and a second breakdown in a new place may occur 511.

To achieve such control, some disclosed embodiments may include plasma reactor design elements that can provide tangential gas velocity in certain regions inside the reactor. This tangential gas velocity may be exploited for causing and controlling displacement of hot and excited gas traces in order to control the location of subsequent breakdowns. The disclosed embodiments may also include a plasma channel design including devices for causing and/or controlling gas swirling in regions inside the plasma channel.

The disclosed embodiments may also include multichannel designs for facilitating system scalability and increasing electric efficiency.

DETAILED DESCRIPTION

Further development of plasma chemical reactors based on hot plasma pulse electric discharge in gas flow involves several challenges associated with energy efficiency including energy efficiency of energy transfer from power supply to plasma, electrode lifetime and system scalability. The disclosed embodiments and techniques may provide an ability to cause the plasma filament to jump from one electrode point to another with each pulse, to stabilize voltage of breakdowns at a suitably high enough level, to provide efficient energy transfer from power supply to plasma, and/or to scale the plasma reactors up to any desirable capacity, among other potential features. The disclosed embodiments may also offer significantly improved electrode lifetimes.

Figure 1:
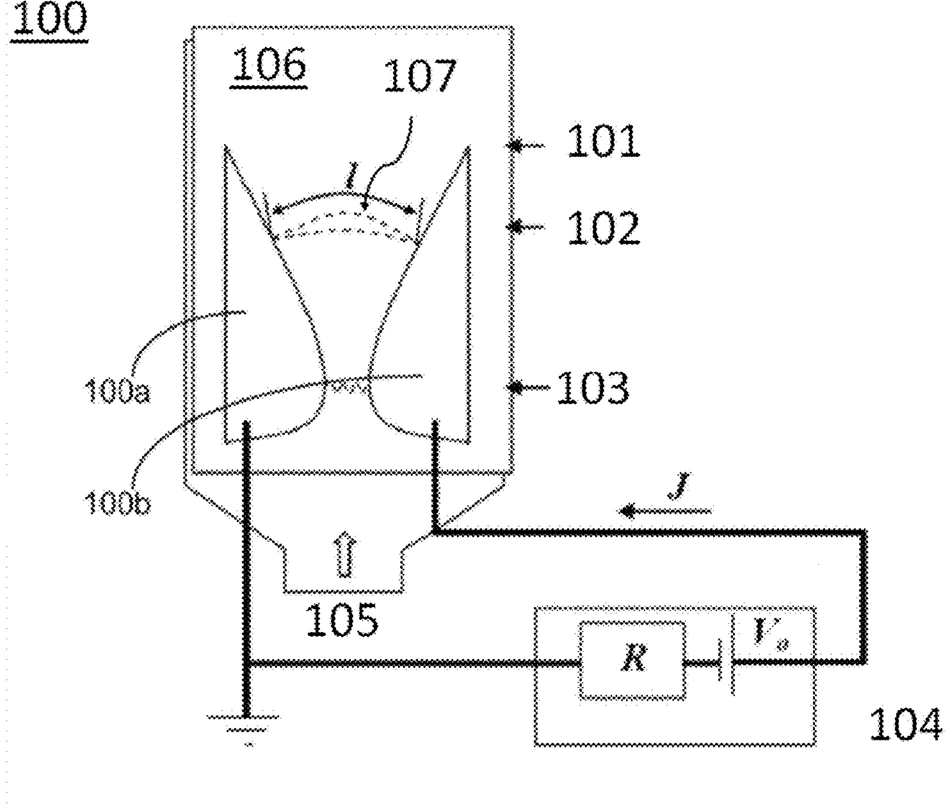
FIG. 1 shows a gliding arc geometry and plasma filament stretching mechanism.
Figure 2:
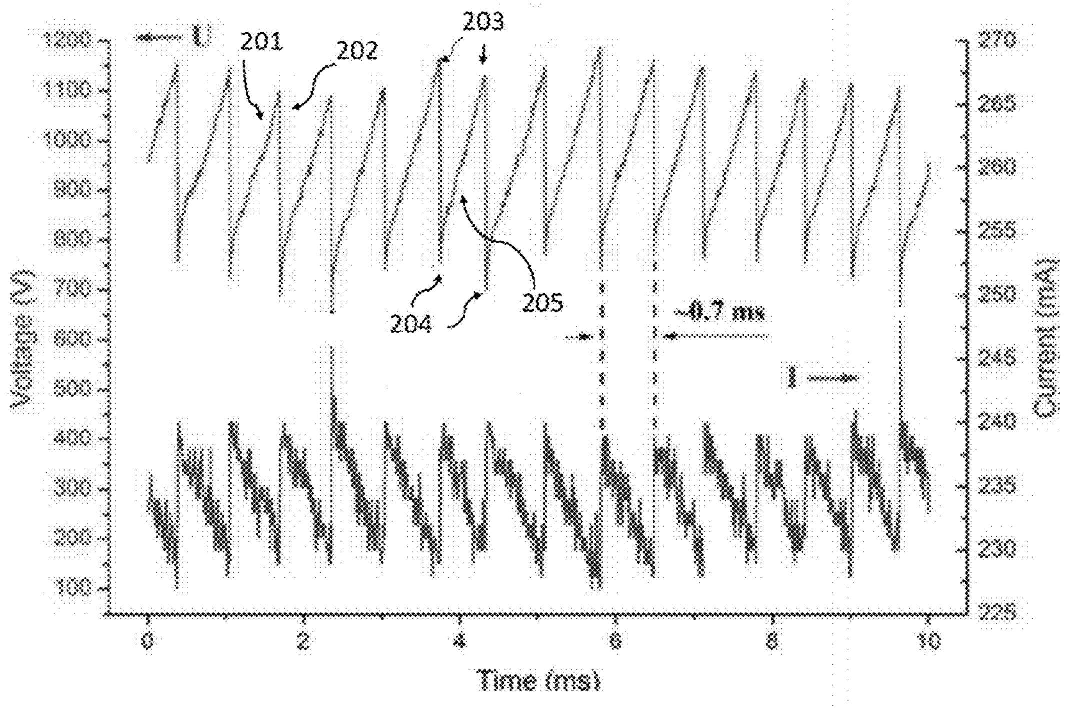
FIG. 2 shows gliding arc voltage and current waveforms.
Figure 3:
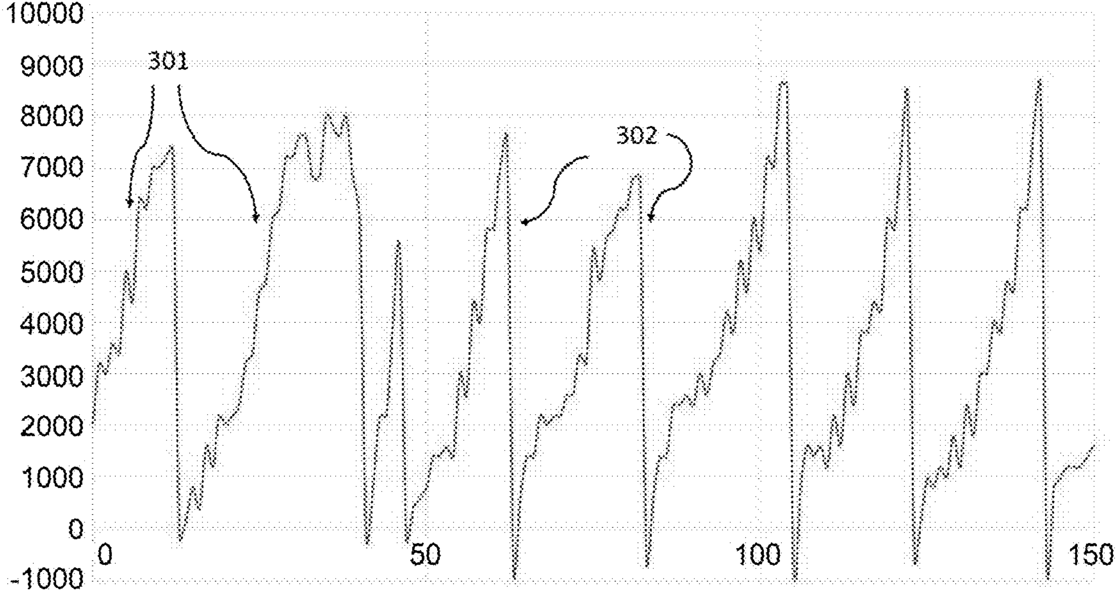
FIG. 3 shows nanosecond hot plasma pulse electric discharge in gas flow.
Figure 4:
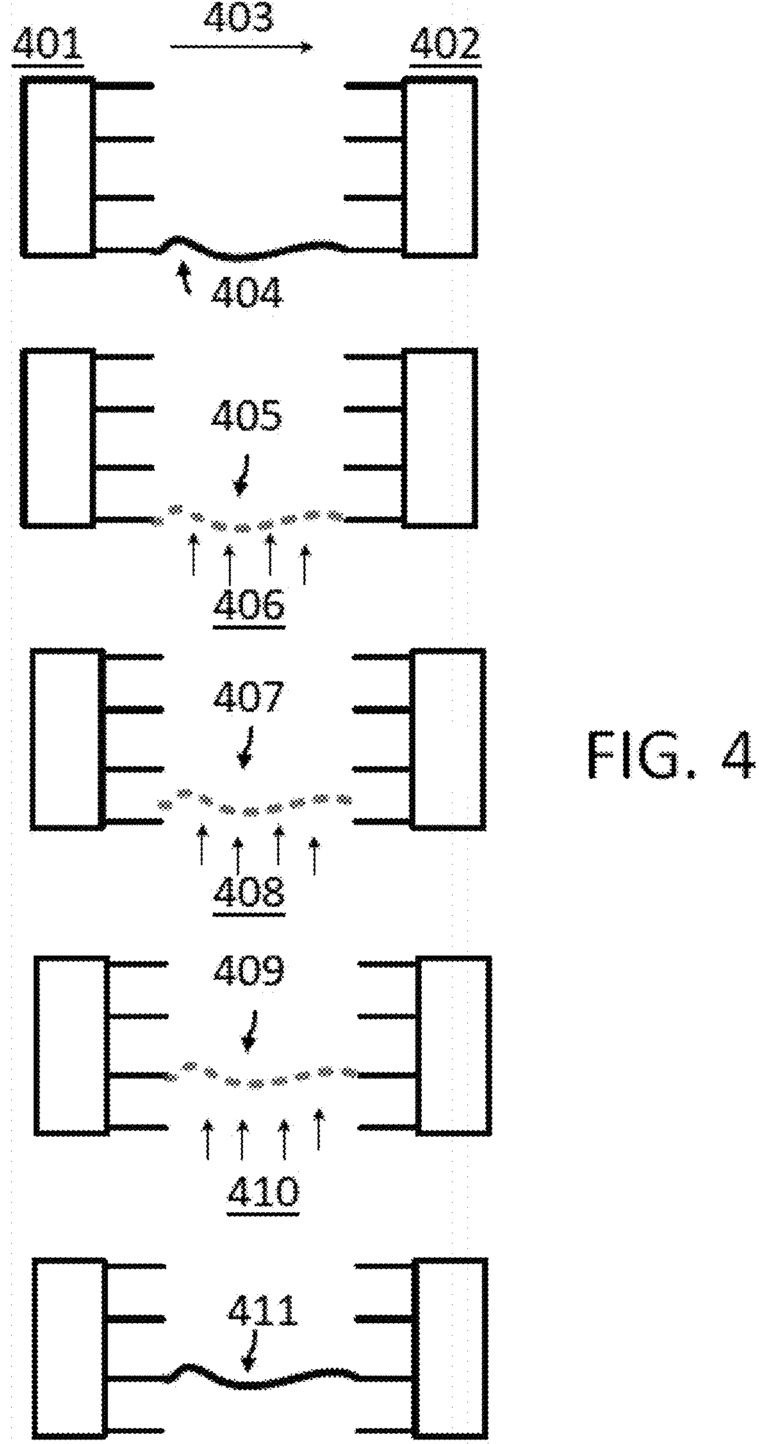
FIG. 4 illustrates aspects of controlling breakdown locations of nanosecond hot plasma pulse electric discharge using tangential gas flow.
Figure 5:
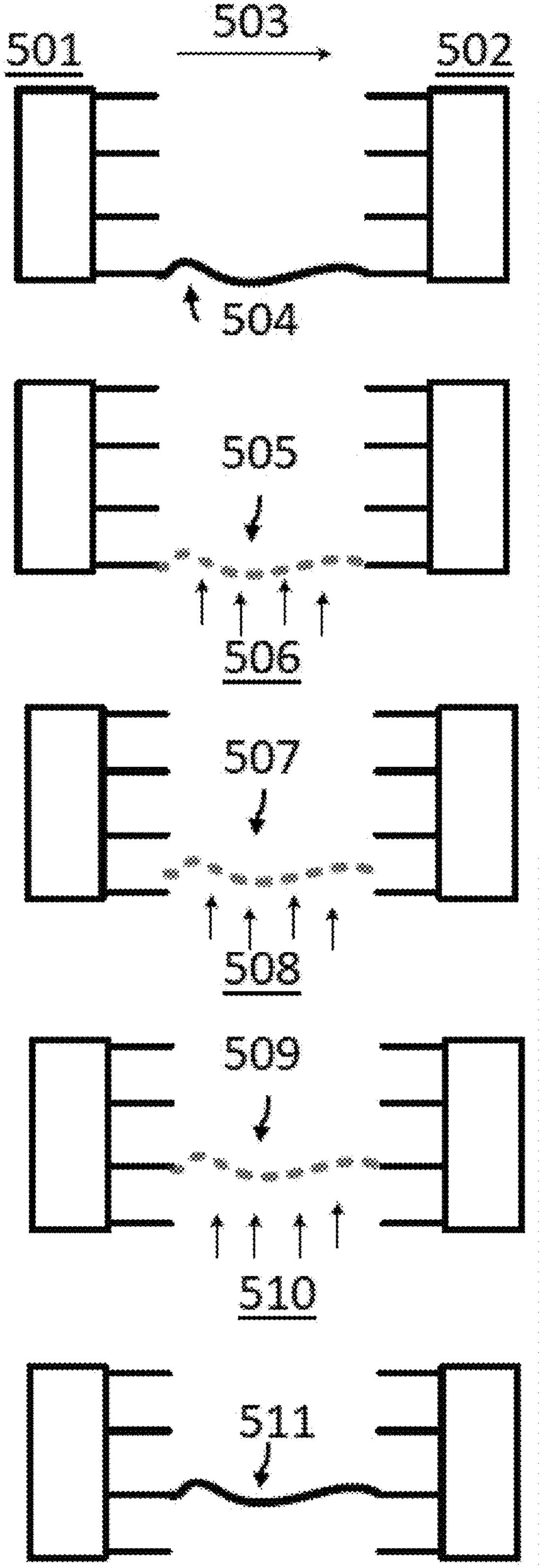
FIG. 5 illustrates aspects of controlling breakdown voltage of nanosecond hot plasma pulse electric discharge using tangential gas flow.
Figure 6:
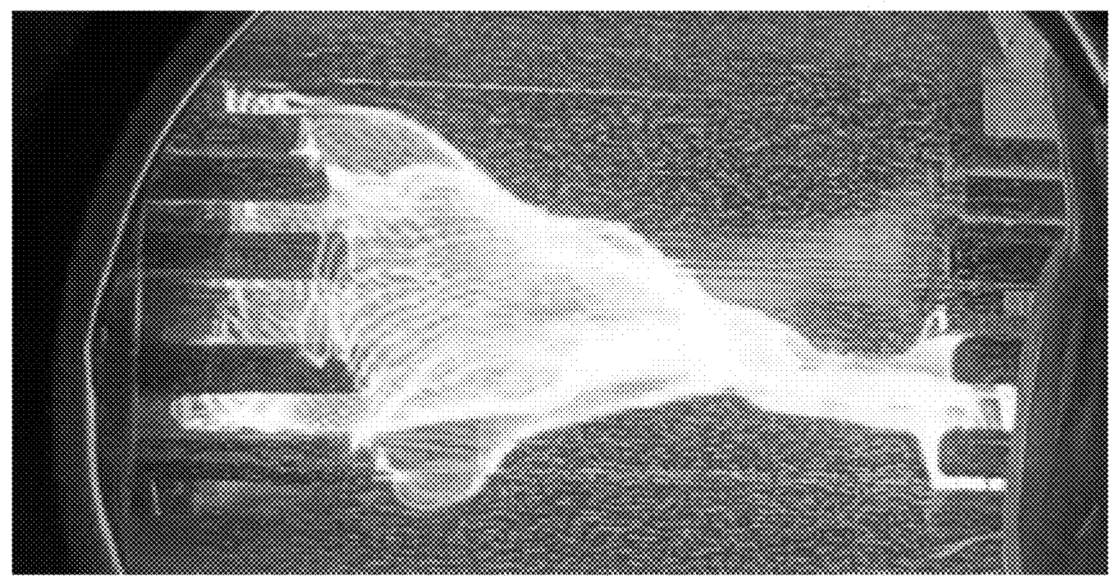
FIG. 6 shows a picture of several serial pulses of nanosecond hot plasma pulse electric discharge affected by tangential gas flow.

To stimulate displacement of new plasma filaments to new locations (relative to previous plasma filament locations), the disclosed embodiments may enable moving of hot and excited gas traces after extinguishing of plasma filaments. Position and parameters associated with a trace from a previous plasma filament determine (or affect) the position and breakdown voltage associated with the next plasma filament. For example, if a first breakdown with a cold gas takes place at a voltage of about 30 kV, a next breakdown may take place at three time less voltage (about 10 kV) because of the existence of a hot and excited gas trace. Therefore, control of hot and excited gas traces from previous pulses can be important for controlling subsequent plasma filament parameters and position. Such control can enable jumping of the plasma filament from one electrode point to another with each pulse to prevent overheating and melting of certain electrodes points, which can significantly increase electrode life. Such control can also be important for stabilizing the breakdown voltage, as local gas overheating may result in varying (e.g., decreased) breakdown voltages associated with locations where such local gas overheating occurs. An example of such behavior of plasma filaments is shown in FIG. 6.

One factor for controlling the new breakdown location in nanosecond hot plasma electric discharge, which is affected by residual hot and excited gas trace after a previous pulse, is to move this trace a certain distance before a next breakdown occurs. In some cases, this movement may include translation in a perpendicular direction relative to a previous filament. To provide such movement, the disclosed embodiments may provide perpendicular tangential gas velocity in a certain region of the plasma channel. In some cases, this tangential velocity $V_{tang}$ may be more than $V_{tang}>f*10^{-3}$ m/s where f is electric discharge pulse frequency and displacement $10^{-3}$ m is characteristic distance between neighbor electrodes pins. At a typical frequency of 50 kHz, the disclosed embodiments may provide a tangential velocity of about 50 m/s. To provide this velocity, the disclosed embodiments may include swirling devices in the plasma channel. In some cases, gas swirling systems may be included on the input and output of the channel. The disclosed embodiments may include any suitable design for providing the described tangential gas flow velocity. In some cases, an electrodes isolator having an auger shape may be used for anode and cathode isolators (see FIG. 7 and FIG. 8).

Figure 7:
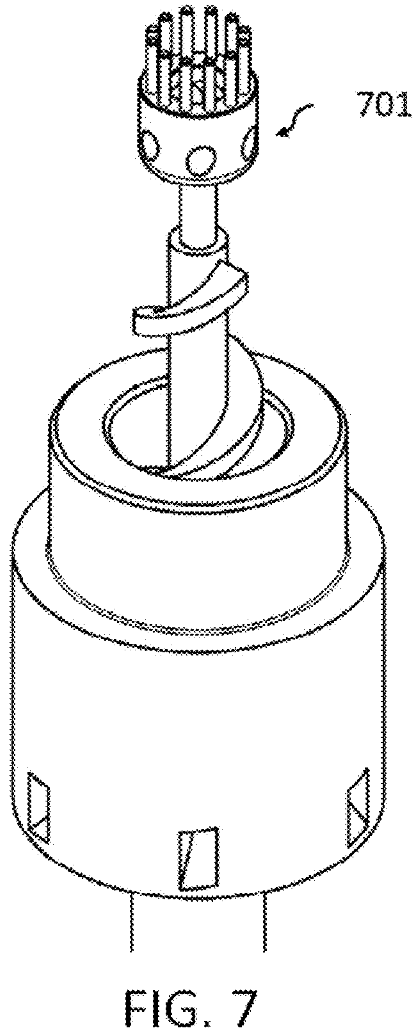
FIG. 7 shows an anode design with auger shaped isolator of nanosecond hot plasma pulse electric discharge with tangential gas flow, according to exemplary disclosed embodiments.

Other configurations for enabling and controlling gas swirling in a plasma channel may include tangential holes (701) in anode electrodes themselves as shown in FIG. 7. Such configurations can provide desirable tangential velocity in locations, such as those close to electrodes ends, which can be important in controlling the movement of plasma filament locations from pulse to pulse.

Figure 8:
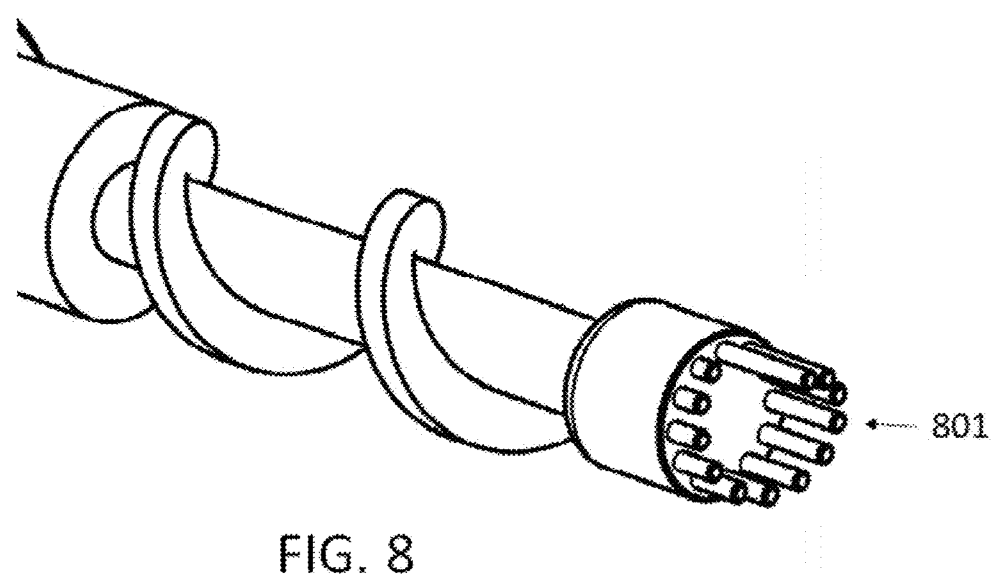
FIG. 8 shows a cathode design with variable pins length and auger shaped isolator of nanosecond hot plasma pulse electric discharge with tangential gas flow, according to exemplary disclosed embodiments.
Figure 9:
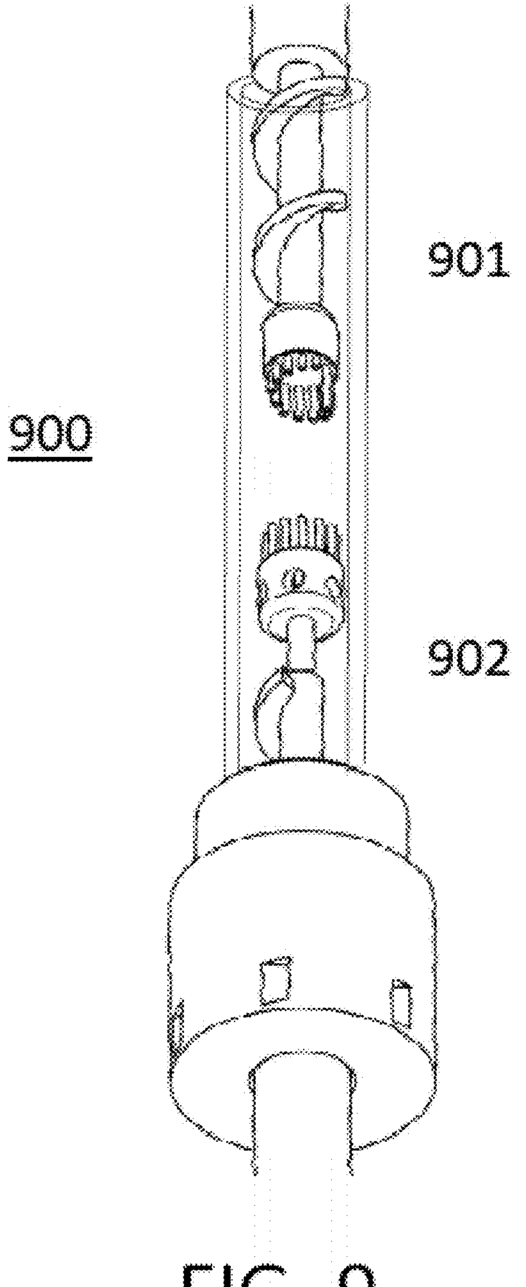
FIG. 9 shows a plasma channel with anode and cathode assembly of nanosecond hot plasma pulse electric discharge with tangential gas flow, according to exemplary disclosed embodiments.

Some disclosed embodiments may also include electrode configurations to enable voltage control (e.g., maintaining certain minimum breakdown voltage levels, avoiding significant drops in breakdown voltages, etc.) and stabilization. In some cases, such configurations may include variable length electrode pins. An exemplary cathode including variable length electrode pins (801) is shown in FIG. 8. An exemplary anode including tangential holes (902) and a cathode including variable pin lengths (901) assembled on auger shaped isolators in a cylindrical plasma channel (900) is shown in FIG. 9. Such configurations may provide a stable voltage, among other operational characteristics favorable for stimulation of plasmachemical reactions.

Figure 10:
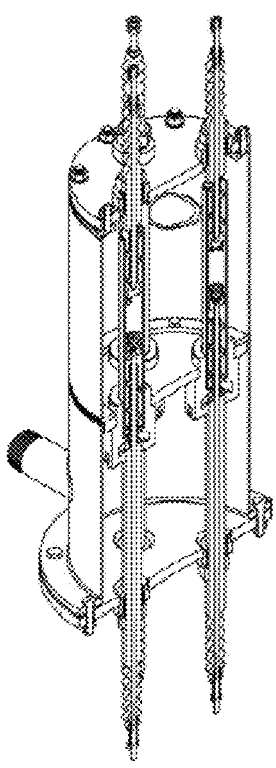
FIG. 10 shows a plasma reactor with four channels of nanosecond hot plasma pulse electric discharge with tangential gas flow, according to exemplary disclosed embodiments.

Features of the disclosed embodiments, including a multichannel reactor, among others, may enable scaling up to any desired capacity. Such a multi-channel reactor may include any of the described features and operational characteristics described herein for one or more of the channels in the multi-channel reactor. In some cases, many similar parallel channels with a common flow input and output may be employed to provide any desirable reactor capacity. An example of a four-channel reactor is shown in FIG. 10. Each channel has a gas input system with tangential holes configured to promote equalization of gas flow through each channel.

Figure 11:
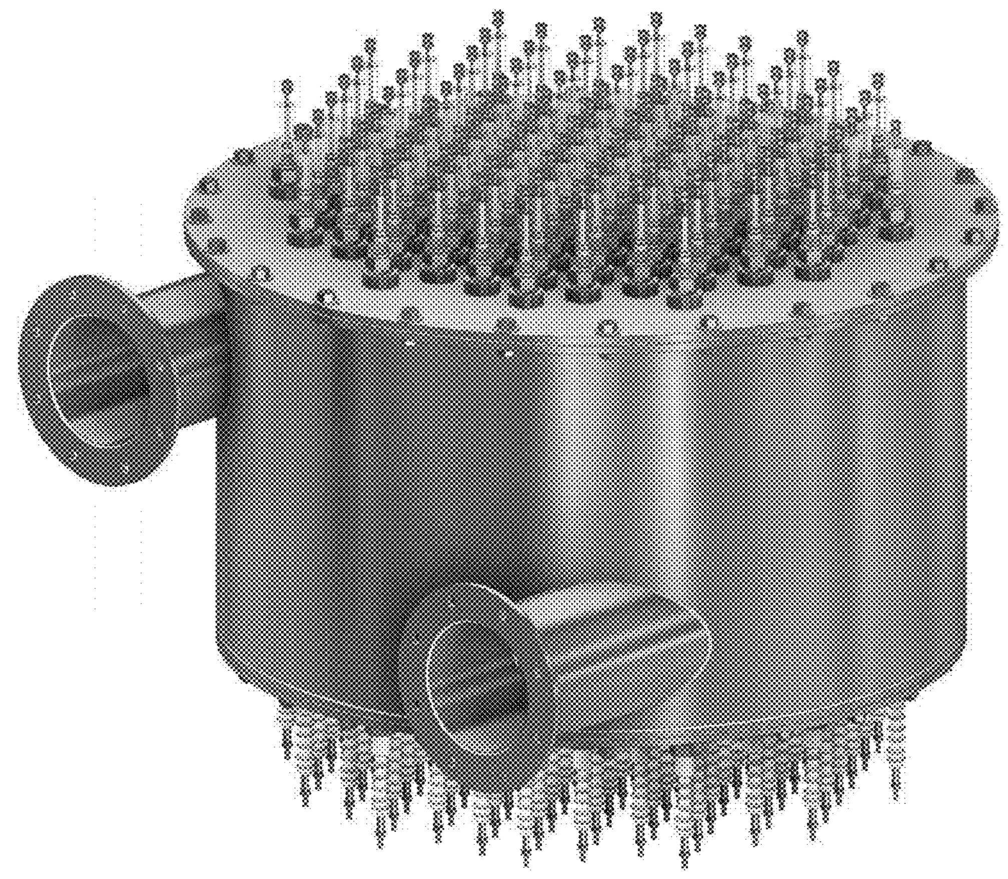
FIG. 11 shows a plasma reactor with 97 channels of nanosecond hot plasma pulse electric discharge with tangential gas flow, according to exemplary disclosed embodiments.

The number of channels included in a multi-channel reactor can be increased to provide a reactor module with any suitable/desirable capacity. Further scaling can be achieved by increasing the number of modules used to form the reactor. One example configuration of a plasma reactor module having 97 plasma channels is shown on FIG. 11.

Figure 12:
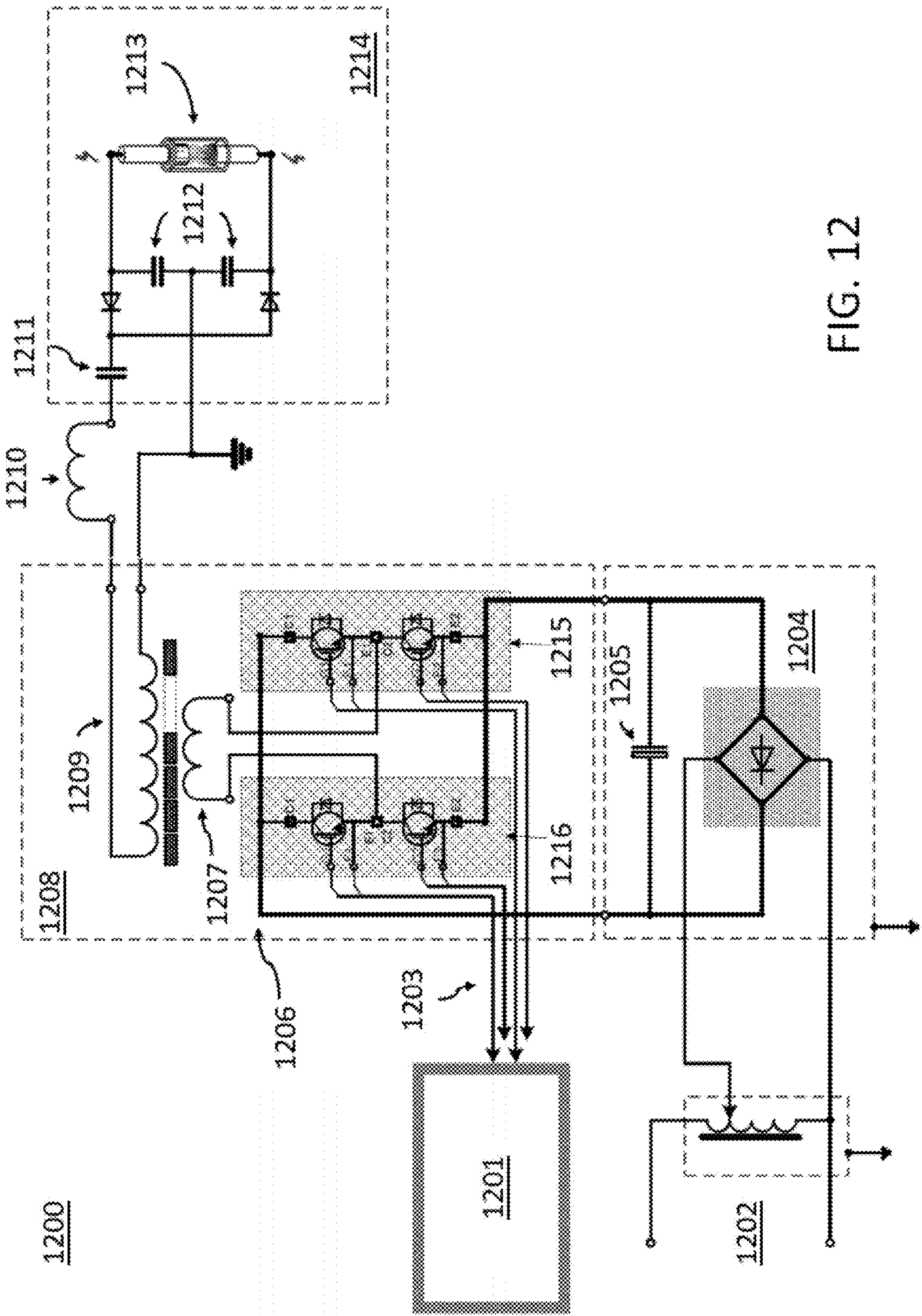
FIG. 12 shows a schematic representation of a plasma reactor with one channel of nanosecond hot plasma pulse electric discharge, according to exemplary disclosed embodiments.
Figure 14:
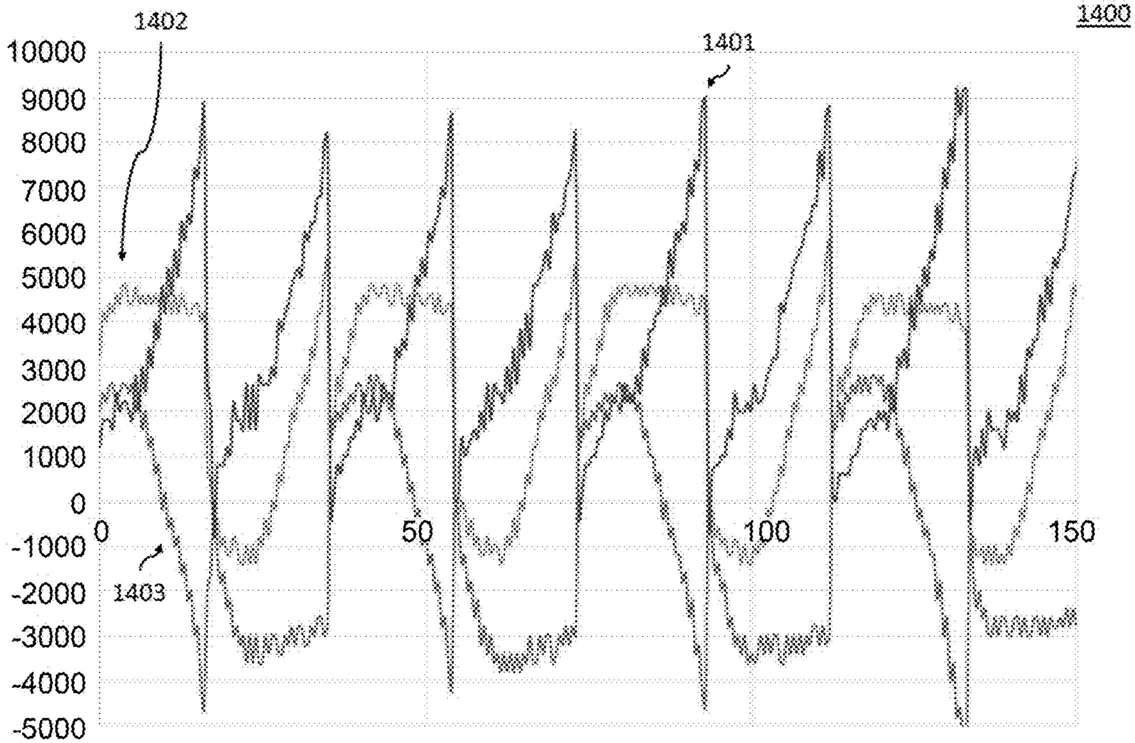
FIG. 14 shows anode, cathode, and total voltage waveforms for exemplary disclosed embodiments.

The stabilization of breakdown voltages offered during operation of the disclosed plasmachemical reactors, for example, by gas swirling elements associated with (e.g., installed directly in) the plasma channel, may have several benefits. In some cases, such stabilization may significantly increase energy efficiency, including energy efficiency of energy transfer from a power supply to the plasma. In some cases, in addition to other techniques described herein, breakdown voltages may be at least partially stabilized using a charging matching circuit provided between a high voltage transformer and the electrodes. Such a circuit is schematically represented by FIG. 12. In FIG. 12, 1201 depicts a driver, 1202 depicts a variac (110V, 20 A), 1203 depicts driver signals, 1204 depicts a diode bridge (4×60EPF12), 1205 depicts a capacitor (6×820 μF, 200V), 1206 is +500V, 1207 depicts a primary winding of three turns, 1208 depicts a power module, 1209 depicts a secondary winding of 220 turns, 1210 depicts an inductor (5.5 mHn), 1211 depicts a capacitor (550 pF), 1212 depicts capacitors (500 pF each), 1213 depicts a plasma channel, 12014 depicts a high voltage rectifier/current stabilizer, 1215 depicts a IGBT module (CM200DU—24NFH), 1216 depicts a IGBT module (CM200DU—24NFH). As illustrated, this circuit may include an inductor and a capacitor connected serially and loaded on two half-wave rectifiers each including a high voltage diode and a capacitor. In some cases, one rectifier may include a positively charged anode, and another rectifier may include a negatively charged cathode. Charging of such a matching circuit may provide voltage oscillation on a flat top of a rectangular pulse of voltage generated by the high voltage transformer. Such oscillations may provide quasi-continual charging in small steps at a characteristic frequency higher (e.g., ten times higher or more) than a frequency of the voltage signal at the high voltage transformer. This quasi-continual charging may reduce or prevent charging energy losses (FIG. 14). In FIG. 14, 1400 is a plot of voltage and time, 1401 corresponds to the total voltage, 1402 corresponds to the anode voltage, and 1403 corresponds to the cathode voltage. In some cases, it may be desirable to achieve a frequency of electric discharge breakdown that is at least two times more than an operational frequency of the transformer. As shown in FIG. 14, the operational frequency of the transformer is about 25 kHz, but electric discharge breakdowns are stabilized at a frequency of about 50 kHz. The described quasi-continual charging process may reduce or minimize charging energy losses. In the schematic shown in FIG. 14, a high voltage transformer powered by an IGBT bridge was used. Other examples, however, may include a fly-back and/or push-pull semi bridge configuration. Further, other transistor types may also be used.

Figure 15:
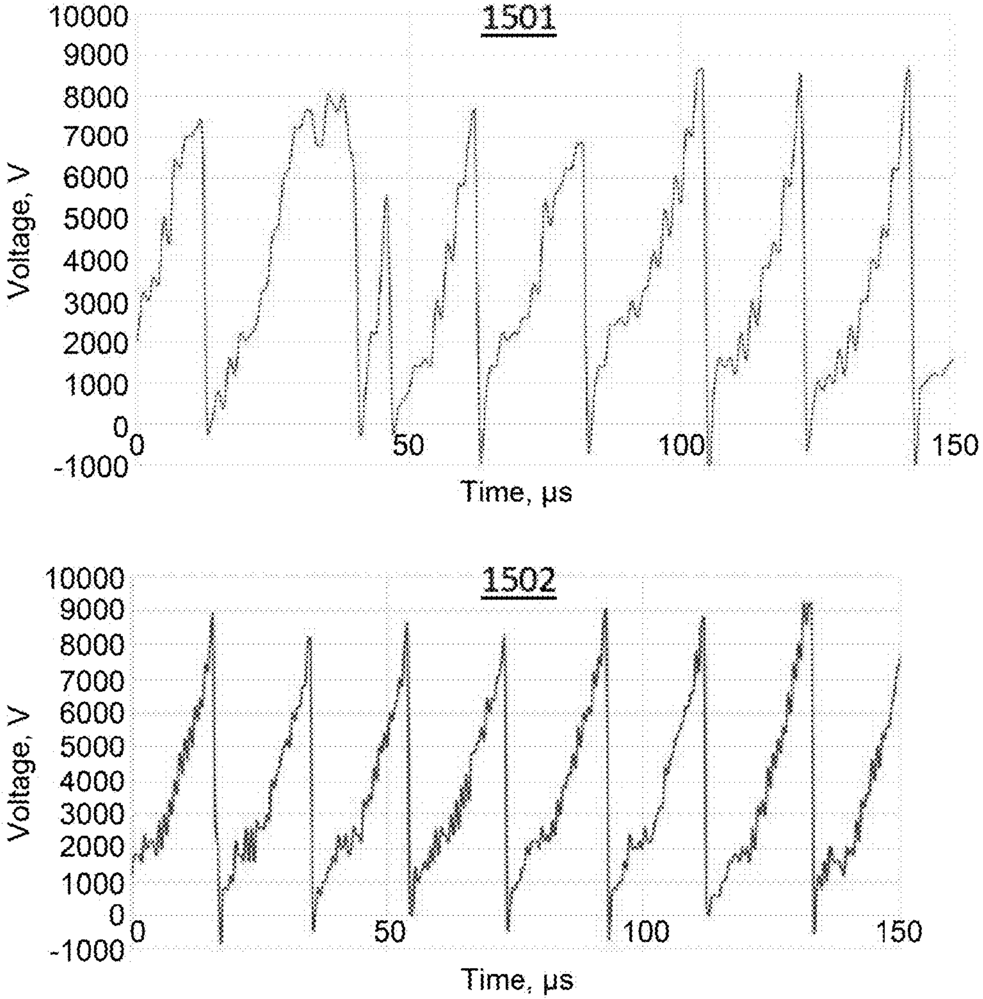
FIG. 15 shows a total voltage waveform for designs with auger shaped electrodes, additional gas swirling system, and variable length cathode pins, according to exemplary disclosed embodiments, and shows a total voltage waveform for a design without these modifications.

The described matching circuit between the high voltage transformer and electrodes may also be used for splitting power from one high voltage transformer and invertor into a desired number of channels. An example of such a splitting arrangement (e.g., splitting into four channels) is shown in FIG. 15. In FIG. 15, 1501 depicts a plot of voltage with time corresponding to a design without modified gas swirling and voltage increasing system, 1502 depicts a plot of voltage with time corresponding to a design auger shaped electrodes, an additional gas swirling system, and variable length cathode pins. While the example shown in FIG. 15 includes a split into four channels, other quantities of channels may be provided in a similar way. The described stabilization and control of breakdown voltage of plasma channels, associated with the described configurations for promoting gas swirling inside the plasma channels, may significantly increase the operational efficiency (among other benefits) of simultaneously operation of several different plasma channels powered by a single high voltage transformer and inverter. Further, the described configurations and techniques may facilitate breakdown voltage stabilization, reduce or minimize charging energy losses, enable system capacity scalability up to any desirable number of plasma channels, and increase efficiency of plasma-chemical reactors.

The presently disclosed embodiments may also include one or more features, or may be used in one or more processes, as described in the sections below.

Plasma may provide a powerful instrument for carrying out of chemical reactions with high activation energy such as for example syn gas production, CO2 dissociation, H2S dissociation and so on. But regular plasma technologies, such as electric arc or microwave electric discharge, may have some disadvantages for plasma chemical applications. For example, there may be challenges with these types of systems in maintaining conditions for carrying direct chemical reactions (e.g., chemical reactions which transmit initial reagents to substances) while avoiding reverse chemical reactions. In plasma chemistry, this may be referred to as quenching, which includes rapid removal of reaction products from a high temperature reaction zone.

The disclosed approach may provide an efficient solution for quenching. Electric discharge of this type may include a series of electrical breakdowns of gas which may be observed as thin needles that appear and extinguish, e.g., each time in new place. In this way, initial reagents can be treated in order to create desirable products and practically avoid reverse chemical reactions by fast extinguishing of plasma channels. Frequency of such breakdowns can be up to 100 kHz providing efficient of treatment of high gas flows.

Figure 16:
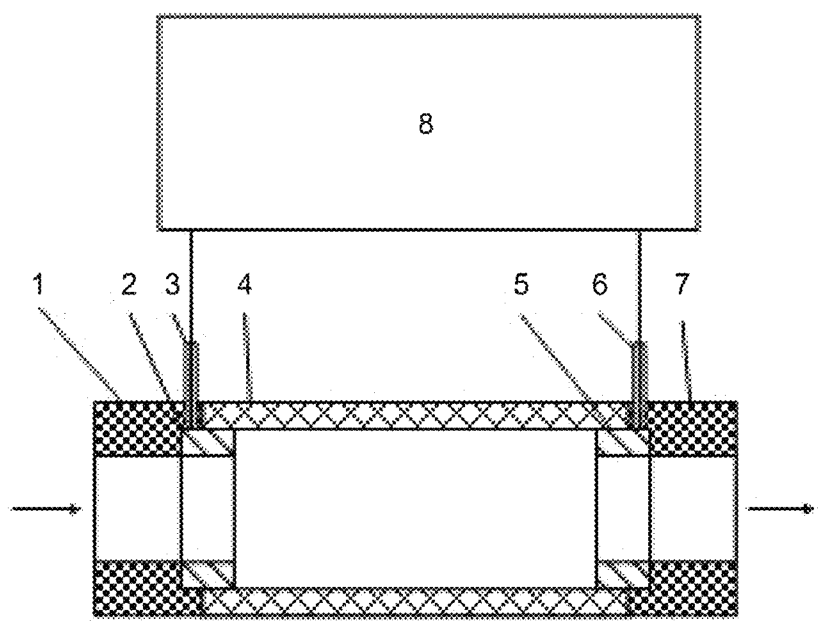
FIG. 16 depicts a plasma chemical reactor consistent with some embodiments.

FIG. 16 depicts an exemplary plasma chemical reactor based on a principle of generation and extinguishing of hot plasma channel between anode and cathode with high frequency. FIG. 16 depicts a gas input module (1), anode (2), anode high voltage connector (3), discharge chamber (4), cathode (5), cathode high voltage connector (6), gas output module (7) and high voltage power supply with special electric characteristics.

Figure 17:
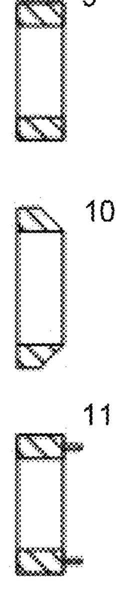
FIG. 17 depicts exemplary electrode configurations.

One or both of the cathode and anode can have a disc shape as depicted in FIG. 17 (9). In some cases, the anodes and cathodes may have a disc shape with a sharp end or a shape of a disc with several needles.

A plasma chemical reactor based on a principle of generation and extinguishing of a hot plasma channel between an anode and cathode with high frequency may include gas input module FIG. 16 (1), anode FIG. 16 (2), anode high voltage connector FIG. 16 (3), discharge chamber FIG. 16 (4), cathode FIG. 16 (5), cathode high voltage connector FIG. 16 (6), gas output module FIG. 16 (7) and high voltage power supply with output capacitor C with capacitance not less than: capacitance (nF)>average current (A)*100.

Additionally, an exemplary disclosed system may recycle gas by an additional gas pump for increasing gas velocity through discharge zone independently on feed gas flow.

The disclosed system may include an additional high voltage capacitor installed parallel to the output connectors of power supply FIG. 16 (8).

An exemplary disclosed system may direct the flow of the working gas from the anode to the cathode (or vice versa).

Figure 18:
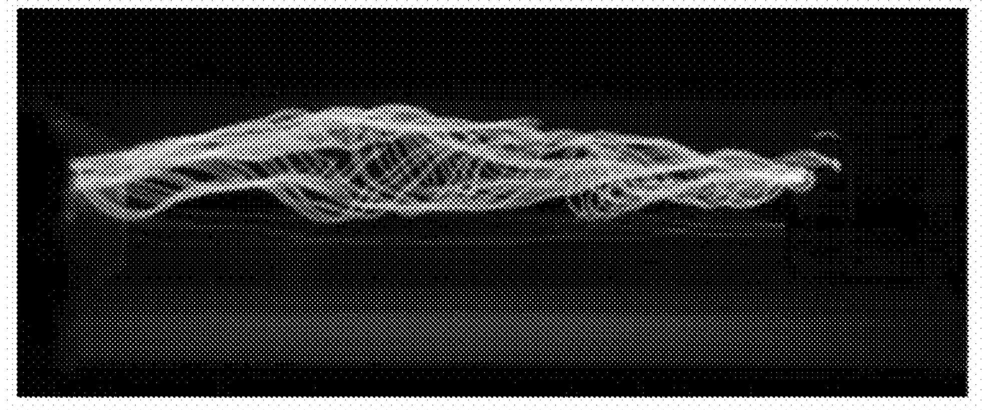
FIG. 18 depicts an electric discharge image consistent with some embodiments.

FIG. 18 depicts an electric discharge image consistent with exemplary disclosed embodiments.

In an exemplary disclosed systems, either or both of the cathode and anode shapes and materials may include one or more of:

- a disk;
- a disk with a sharp edge;
- a disk with several needles; and
- a cone with through holes; in a variety of combinations.

In some embodiments, Bronze BRX, tungsten, titanium, and molybdenum can be used as electrode materials.

Set up of the exemplary disclosed systems may include any combination of:

- tuning a rate of flow of working gas through the spark discharger;
- adjusting working gas pressure in the discharger;
- varying a distance between the electrodes; and
- varying a discharge voltage between the electrodes.

Exemplary features of the disclosed plasma reactors include: a high electric efficiency, improved energy efficiency of plasma-chemical processes (minimal energy cost), a robust and reliable electrode design providing extended lifetime which may reduce the need for replacing parts, and an extremely compact plasma reactor design.

Figure 19:
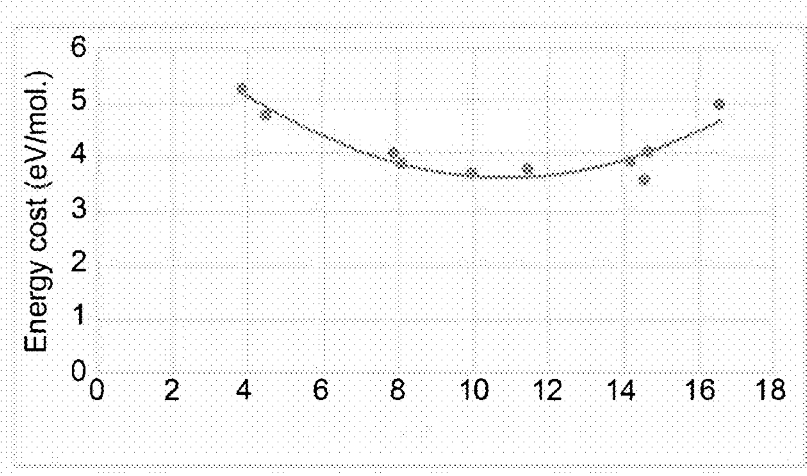
FIG. 19 depicts experimental results of CO2 dissociation in an exemplary plasma converter.

Exemplary uses for the disclosed systems include $CO_2$ dissociation. FIG. 19 depicts $CO_2$ dissociation in an exemplary plasma converter. An exemplary $CO_2$ dissociation process can be used for: reduction of $CO_2$ in an exhaust gases (e.g. $CO_2$ emission reduction), $CO_2$ conversion to liquid fuel (e.g. $CO_2$ emission reduction), oxygen generation from $CO_2$ for space applications, and hydrogen production (replacement of electrolysis process).

Also disclosed are methods of syngas production (e.g., from $CH_4/CO_2$ mixture). Exemplary processes can be used for: $CO_2/CH_4$ conversion for hydrogen production and/or $CO_2$ conversion to liquid fuel using electric energy and methane. Syngas may be produced from a $CH_4/CO_2$ mixture.

Figure 20:
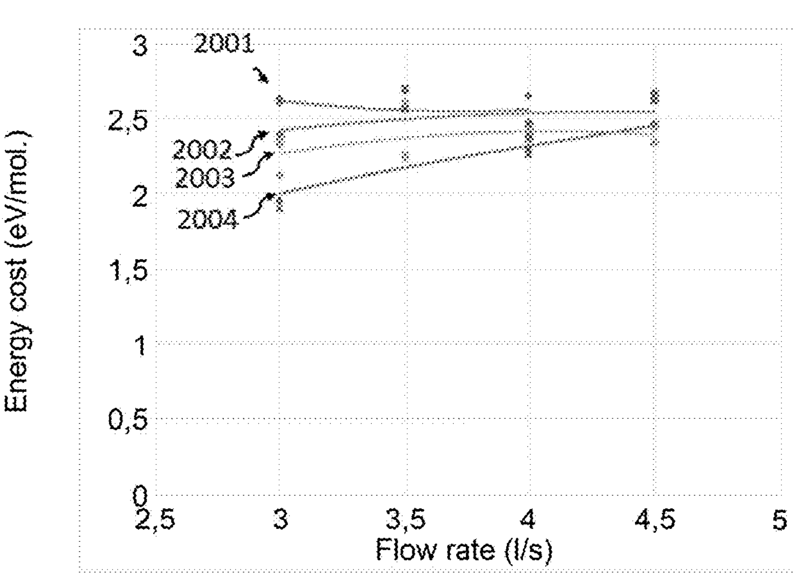
FIG. 20 depicts experimental results of CO2/CH4 mixture conversion in an exemplary plasma converter.

FIG. 20 depicts experimental result of an exemplary $CO_2/CH_4$ mixture conversion in a plasma converter to CO and $H_2$ and dependence of energy cost on flow rate for different mixture compositions. In FIG. 20, 2001 corresponds to a $CH_4/CO_2$ rate of 1.46, 2002 corresponds to a $CH_4/CO_2$ rate of 0.45, 2003 corresponds to a $CH_4/CO_2$ rate of 0.95, and 2004 corresponds to a $CH_4/CO_2$ rate of 0.67.

Figure 21:
FIG. 21 depicts solid sulfur scaled on reactor walls during an exemplary H2S dissociation test.

Also disclosed are methods of hydrogen sulfide ($H_2S$) dissociation. $H_2S$ conversion is one of the key processes in Oil & Gas refinery plants. Technology based on the convention Claus process has significant disadvantages (major one—hydrogen generated for the process converts into $H_2O$ and therefore is lost). By contrast, an exemplary plasma process of $H_2S$ dissociation to hydrogen and sulfur may be more efficient if energy cost of dissociation is about 1 eV/molecule of $H_2S$. In some embodiments, a plasma process converts $H_2S$ into two useful products—hydrogen (which may be recovered) and solid sulfur. After hydrogen sulfide ($H_2S$) dissociation, solid sulfur may be melted off of the reactor walls. Sulfur can be removed from gas flow by electrostatic precipitation. FIG. 21 depicts solid sulfur scaled on reactor walls during $H_2S$ dissociation tests.

Technology of plasma conversion of gas mixtures may offer an efficient tool for many potential applications, including $CO_2$ utilization (such as $CO_2$ emission reduction) and hydrogen production. The exemplary disclosed system may offer advantages such as:

- energy efficiency
- operation costs
- simple, reliable, and compact design.

An exemplary disclosed system may also be used for converting ethane to ethylene or propane to propylene, according to, e.g.: $C_2H_6 \rightarrow C_2H_4+H_2$ and $C_3H_8 \rightarrow C_3H_6+H_2$.

Further, the exemplary disclosed systems may be used to convert butane and/or isobutene to butylene and isobutylene. For example, $C_4H_{10} \rightarrow C_4H_8+H_2$.

Additionally, the disclosed systems may be used to synthesize acetylene. For example, $CH_4$ ($C_xH_{2x+2}$ in general)$\rightarrow C_2H_2+2H_2$.

In some embodiments, the disclosed system may be used to produce hydrogen gas (e.g., for use in refueling hydrogen fuel cells).

Figures 22, 23:
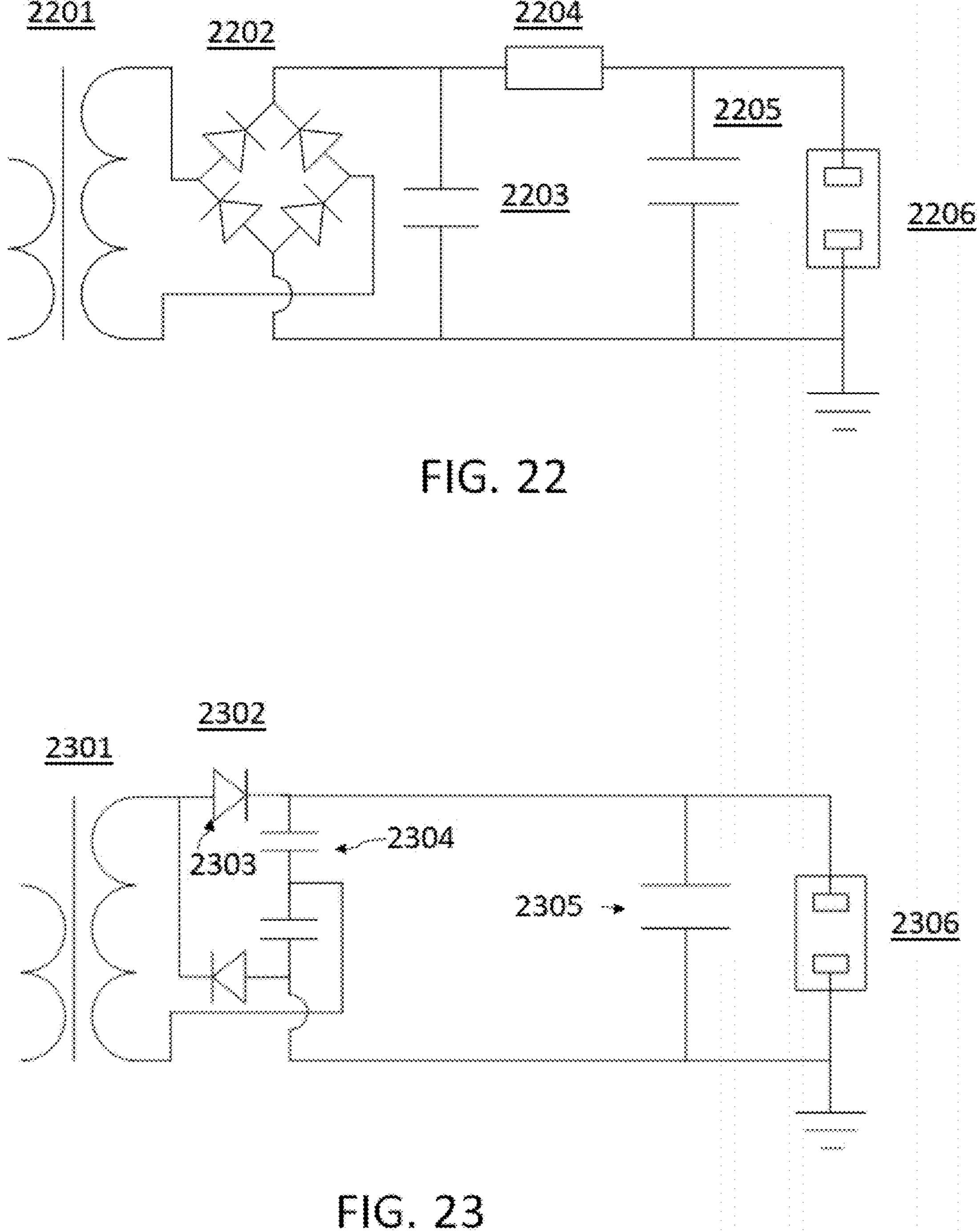
FIG. 22 depicts an exemplary plasma reactor and associated components.
FIG. 23 depicts an exemplary plasma reactor and associated components.

The plasma reactors disclosed herein may have a variety of configurations. In some embodiments, the plasma reactor may be associated with or may include various components for providing one or more aspects of the functionality of the plasma reactor. Such components may include, without limitation, one or more power supply units, power supply circuitry, gas flow regulators, sensors, etc. Such components may also include one or more processing units (e.g., a microcontroller or other type of logic device) for automatically controlling or implementing one or more functions of the plasma reactor. Such processing units may control plasma filament generation and/or plasma filament timing through automatic control of various power supply components (e.g., based on feedback received at the control unit), circuit elements, gas flow regulation devices, etc. While the disclosed plasma reactors may be automatically controlled through the use of one or more logic-based controllers, in some embodiments, the disclosed plasma reactors may be implemented using analog electronic components. One such example for generating and extinguishing a described plasma filaments is shown in FIG. 22. In FIG. 22, 2201 depicts a high voltage transformer, 2202 depicts a high voltage diode bridge, 2203 depicts a rectification capacitor, 2204 depicts a high voltage resistor, 2205 depicts a pulse output capacitor, and 2206 depicts a plasma chemical reactor.

In this the example of FIG. 22, a high voltage transformer and diode bridge may provide a high voltage on a rectification capacitor. A high voltage resistor may control or provide a desired level of current for charging of a pulse output capacitor. After charging up to voltage which is enough for breakdown of electrodes of plasma chemical reactor, the pulse output capacitor may discharge through a plasma channel in the plasma chemical reactor to form a plasma filament. Upon a change in polarity, the plasma filament may be extinguished by gas flow. The process of plasma filament generation and subsequent extinguishing of the plasma filament may be repeated continuously over any desired time period.

Various voltages and resistances may be used in the plasma reactor and associated electronics components described above. In one example, an experimental setup included use of an output voltage of 60 kV applied at the rectification capacitor. The high voltage resistor was 100 kOhm. The pulse output capacitor was 350 pF. With these components, the resulting plasma filament generation/extinguish cycle has a frequency of about 60 kHz. The effective inductance of the circuit for discharging of pulse output capacitor through plasma chemical reactor was 0.5 uHn. Current pulse duration and plasma filament lifetime was about 150 ns.

Another example of a plasma reactor and associated components appears in FIG. 23. In FIG. 23, 2301 depicts a high voltage high frequency transformer, 2302 depicts a voltage multiplier, 2303 depicts a high voltage diode, 2304 depicts a high voltage capacitor, 2305 depicts a pulse output capacitor, and 2306 depicts a plasma chemical reactor.

A high voltage transformer and voltage multiplier scheme based on diodes and capacitors may provide desirable current charging of pulse output capacitor. After charging up to a voltage which is enough for breakdown, the plasma chemical reactor pulse output capacitor may discharge through a plasma channel to form a plasma filament. At the moment of changing polarity (or at some time after a change in signal polarity), the plasma filament may be extinguished by gas flow. The process may be repeated continuously.

In one example, an experimental setup included 100 pF multiplier capacitors. A high frequency high voltage transformer was operated at 30 kHz and 60 Hz frequency respectively. Pulse output capacitor was 300 pF. As a result, plasma pulses frequency was 30 kHz and 60 kHz respectively. Effective inductance of circuit of discharging of pulse output capacitor through plasma chemical reactor was 0.5 uHn, 0.125 and 0.03 uHn respectively. Current pulse duration and plasma filament lifetime was 180 ns, 80 ns and 30 ns respectively.

Some additional exemplary embodiments include the following.

Exemplary Reactor Having a Longer OFF Time than ON Time

In some embodiments, a plasma reactor may repetitively generate and extinguish plasma filaments such that a dwell time during which no plasma filament is present (OFF time) is significantly longer than a plasma discharge interval when the plasma filament is present (ON time). In some embodiments, a longer OFF time may be important in allowing subsequent filaments to follow paths different from their predecessors (leading to increased efficiency).

In some embodiments is a plasma reactor for converting at least one chemical species to one or more reaction products, the plasma reactor comprising: a pair of electrodes; a gas inlet configured to deliver a gas to a location of the pair of electrodes; and a power supply configured to cause a time-varying voltage across the pair of electrodes, wherein the time-varying voltage is configured to cause generation of a plasma filament between the pair of electrodes during each of a plurality of sequential discharge intervals, such that each of the plurality of discharge intervals is separated in time from another of the plurality of discharge intervals by a dwell interval during which no plasma filament is present between the pair of electrodes, and wherein an average dwell interval time is at least ten times longer than an average discharge interval time.

In some embodiments is a plasma reactor for converting at least one chemical species to one or more reaction products, the plasma reactor comprising: a pair of electrodes; a gas inlet configured to deliver a gas to a location of the pair of electrodes; a power supply configured to cause a time-varying voltage across the pair of electrodes; and at least one processor configured to: control the power supply to generate a plasma filament between the pair of electrodes during each of a plurality of sequential discharge intervals, such that each of the plurality of discharge intervals is separated in time from another of the plurality of discharge intervals by a dwell interval during which no plasma filament is present between the pair of electrodes, and wherein an average dwell interval time is at least ten times longer than an average discharge interval time.

In some embodiments, the at least one processor is configured to control energy supply to the pair of electrodes in order to cause the plasma filaments to ignite and extinguish at least 50,000 times per second over a period of at least 10 minutes.

In some embodiments, the duration of each of the plurality of discharge intervals is substantially the same.

In some embodiments, a ratio of an average duration of the dwell intervals to an average duration of the discharge intervals is at least 50.

In some embodiments, a ratio of an average duration of the dwell intervals to an average duration of the discharge intervals is at least 100.

In some embodiments, a duration of at least one of the plurality of discharge intervals differs from a duration of another of the plurality of discharge intervals.

In some embodiments, the at least one processor is configured to control the power supply to cause an average duration of the plurality of discharge intervals to be between about 50 nanoseconds and 200 nanoseconds, and to cause an average duration of the dwell intervals to be between about 500 nanoseconds and 15,000 nanoseconds.

In some embodiments, a distance between the pair of electrodes is between about 2 cm and 10 cm.

In some embodiments, a distance between the pair of electrodes is between about 5 cm and 7 cm.

In some embodiments, an average diameter of the plasma filament generated during each discharge interval is between about 50 micrometers and 1000 micrometers.

In some embodiments, at least one electrode of the pair of electrodes includes one or more needle structures extending from a surface on a distal end thereof.

In some embodiments, at least one electrode of the pair of electrodes includes hafnium.

Exemplary Deactivating Plasma Filament in Order to Reduce Back Reactions

In some embodiments, after a plasma filament causes a chemical reaction to occur, the plasma filament is extinguished for a sufficient period of time so that a back reaction does not occur.

In some embodiments including a plasma generator for facilitating chemical reactions, the plasma generator may include: a reaction chamber; an anode and a cathode in the reaction chamber, connected to a circuit for delivering energy across the anode and cathode; a gas flow inlet for supplying at least one reactant gas to a region of the anode and cathode; a valve for controlling reactant gas flow through the gas flow inlet, wherein the valve is configured to regulate an amount of reactant gas entering a region of the anode and cathode; a power supply configured to deliver energy to the circuit and to regulate energy delivery in cycles such that a first average cycle time when energy is not delivered to the circuit is sufficiently greater than a second average cycle time when energy is delivered to the circuit in order to limit back reactions following the chemical reactions.

In some embodiments including a plasma generator for facilitating chemical reactions, the plasma generator may include: a reaction chamber; an anode and a cathode in the reaction chamber, connected to a circuit for delivering energy across the anode and cathode; a gas flow inlet for supplying at least one reactant gas to a region of the anode and cathode; a valve for controlling reactant gas flow through the gas flow inlet; a power supply configured to deliver energy to the circuit; and at least one processor configured to: control the valve to regulate an amount of reactant gas entering a region of the anode and cathode; regulate energy delivery in cycles from the power supply to the circuit such that a first average cycle time when energy is not delivered to the circuit is sufficiently greater than a second average cycle time when energy is delivered to the circuit in order to limit back reactions following the chemical reactions.

In some embodiments, the first average cycle time is at least 50 times greater than the second average cycle time.

In some embodiments, the second average cycle time is less than about 200 ns.

Exemplary High Frequency Plasma Discharge with Intervening Dwell Time

In some embodiments, a disclosed plasma reactor may repetitively generate and extinguish plasma filaments at a high frequency (e.g., greater than 50 kHz or 100 kHz), but with interleaving dwell times between generated plasma filament events. In some embodiments, the high frequency operation and the interleaving dwell times may be important factors in the improved performance over other systems (e.g., microwave plasma systems) that continuously maintain plasma discharge. For example, the high frequency and relatively long dwell times may provide fast quenching of gaseous reaction products, which can lead to improved efficiency.

In some embodiments is a plasma reactor for converting at least one chemical species to one or more reaction products, the plasma reactor comprising: a pair of electrodes; a gas inlet configured to deliver a gas to a location of the pair of electrodes; and a power supply configured to: cause a time-varying voltage across the pair of electrodes in order to generate a series of periodic plasma discharge events between the pair of electrodes, the periodic plasma discharge events being spaced apart in time from one another by a dwell time during which no plasma discharge occurs between the pair of electrodes; and cause the periodic plasma discharge events to occur at a frequency of at least 50 kHz.

In some embodiments is a plasma reactor for converting at least one chemical species to one or more reaction products, the plasma reactor comprising: a pair of electrodes; a gas inlet configured to deliver a gas to a location of the pair of electrodes; a power supply; at least one processor configured to: cause a time-varying voltage across the pair of electrodes in order to generate a series of periodic plasma discharge events between the pair of electrodes, the periodic plasma discharge events being spaced apart in time from one another by a dwell time during which no plasma discharge occurs between the pair of electrodes; and cause the periodic plasma discharge events to occur at a frequency of at least 50 kHz.

In some embodiments, the at least one processor is configured to cause the periodic plasma discharge events to occur at a frequency of at least 100 kHz.

In some embodiments, the at least one processor is configured to cause a duration of the dwell time to be at least ten times longer than an average duration of each plasma discharge event.

In some embodiments, the at least one processor is configured to cause a duration of the dwell time to be at least 100 times longer than an average duration of each plasma discharge event.

In some embodiments, the at least one processor is configured to cause to cause an average duration of each plasma discharge event to be between about 50 nanoseconds and about 150 nanoseconds, and a duration of the dwell time to be at least 1500 nanoseconds.

In some embodiments, an average duration of each plasma discharge event is between about 50 nanoseconds and about 150 nanoseconds, and a duration of the dwell time to be at least 10,000 nanoseconds.

In some embodiments, a distance between the pair of electrodes is between about 2 cm and 10 cm.

In some embodiments, a distance between the pair of electrodes is between about 5 cm and 7 cm.

In some embodiments, the at least one processor is configured to cause each plasma discharge event to result in generation of a plasma filament between the pair of electrodes, and to cause an average radius of the plasma filament to be between about 50 micrometers and 1000 micrometers.

Exemplary Controlled Filament Instability to Provide Intervening Dwell Time

In some embodiments, in the disclosed plasma reactors, periodic instability may be introduced to cause the plasma filaments to be extinguished. The instability is provided by changes in polarity of the voltage signal applied to the electrode pair, which enables the filament to be extinguished, for example, by gas flowing through the reaction chamber.

In some embodiments is a plasma reactor for converting at least one chemical species to one or more reaction products, the plasma reactor comprising: a reaction chamber; a pair of electrodes in the reaction chamber; a power supply configured to cause at least one of a voltage and a current to vary across the pair of electrodes between positive and negative polarity to initiate plasma ignition during periods of positive polarity and to produce instability in generated plasma filaments during respective periods of negative polarity; and at least one gas flow conduit configured to direct gas in a region of the generated plasma filaments in a manner such that the generated plasma filaments are maintained during respective periods of positive polarity of the applied voltage and terminated during respective periods of negative polarity, and after onset of instability in the generated plasma filaments.

In some embodiments is a plasma reactor for converting at least one chemical species to one or more reaction products, the plasma reactor comprising: a reaction chamber; a pair of electrodes in the reaction chamber; a power supply; at least one processor configured to cause at least one of a voltage and a current to vary across the pair of electrodes between positive and negative polarity to initiate plasma ignition during periods of positive polarity and to produce instability in generated plasma filaments during respective periods of negative polarity; and at least one gas flow conduit configured to direct gas in a region of the generated plasma filaments in a manner such that the generated plasma filaments are maintained during respective periods of positive polarity of the applied voltage and terminated during respective periods of negative polarity, and after onset of instability in the generated plasma filaments.

In some embodiments, the at least one processor is configured to cause the instability in the generated plasma filaments to begin as the voltage across the pair of electrodes changes from positive to negative polarity.

In some embodiments, the varying voltage is periodic and wherein a single cycle of the varying voltage includes a positive polarity portion and a negative polarity portion.

In some embodiments, a generated plasma filament is maintained during a discharge time that falls at least partially within the positive polarity portion, and wherein no plasma filament exists between the pair of electrodes during a dwell time that includes the negative polarity portion and a part of the positive polarity portion, wherein the dwell time is longer than the discharge time.

In some embodiments, a generated plasma filament is maintained during a discharge time shorter in duration than a dwell time during which no plasma filament exists between the pair of electrodes.

In some embodiments, the dwell time is at least ten times longer than the discharge time.

In some embodiments, the dwell time is at least 100 times longer than the discharge time.

In some embodiments, the varying voltage has a sawtooth waveform.

In some embodiments, the gas directed in a region of the generated plasma filaments has a flow velocity of between 0.1 and 50 liters per minute.

Exemplary Gas Flow Velocity Controls Filament Ignition and Termination

In some disclosed embodiments, the gas flow velocity may be important in enabling repeated plasma filament ignition and termination. In some embodiments, if the gas flow rate is too high, the filament won't ignite, and if the gas flow rate is too low, the filament will not extinguish. Therefore, gas flow may be controlled.

In some embodiments is a plasma reactor for converting at least one chemical species to one or more reaction products, the plasma reactor comprising: a reaction chamber; a pair of electrodes; a power supply configured to cause a time-varying voltage across the pair of electrodes, the time-varying voltage periodically varying between local maxima and minima; and at least one gas conduit controlled to direct gas into a region of the pair of electrodes at a rate selected to both enable plasma filament generation and to cause termination of the generated plasma filament between successive local maxima of the time-varying voltage.

In some embodiments is a plasma reactor for converting at least one chemical species to one or more reaction products, the plasma reactor comprising: a reaction chamber; a pair of electrodes; at least one processor configured to control a power supply to cause a time-varying voltage across the pair of electrodes, the time-varying voltage periodically varying between local maxima and minima; and at least one gas conduit controlled to direct gas into a region of the pair of electrodes at a rate selected to both enable plasma filament generation and to cause termination of the generated plasma filament between successive local maxima of the time-varying voltage.

In some embodiments, the reactor further comprising a gas valve associated with the gas flow conduit, and wherein the at least one processor is configured to control the gas valve to deliver gas at a rate that causes repeated filament generation and termination.

In some embodiments, the reactor further comprising a sensor that detects at least one of filament generation and termination and which provides output to the processor for regulating the valve.

In some embodiments, the reactor further comprising a sensor that detects gas flow rate and which provides output to the processor for regulating the valve.

In some embodiments, the gas directed in a region of the generated plasma filaments has a flow velocity of between 0.1 and 50 liters per minute.

In some embodiments, the time-varying voltage has a frequency of at least 50 kHz.

In some embodiments, plasma filament generation occurs at a rate of at least 50 kHz.

In some embodiments, the time-varying voltage has a frequency of at least 100 kHz.

In some embodiments, plasma filament generation occurs at a rate of at least 100 kHz.

Exemplary Rotational as Flow to Increase Efficiency

In some embodiments, the gas flow may have a rotational flow component of motion in addition to the primary axial flow component of motion. This rotational flow may be important to the efficiency of the system and may return an efficiency up to five times greater (or more) than tube reactor systems relying upon laminar flow alone.

In some embodiments is a plasma reactor for converting at least one chemical species to one or more reaction products, the plasma reactor comprising: a reaction chamber; a pair of electrodes in the reaction chamber; a power supply electrically connected to the pair of electrodes, the power supply being configured to cause periodic plasma discharge events between the pair of electrodes in response to a time-varying voltage applied across the pair of electrodes, wherein the periodic plasma discharge events are separated in time by dwell time periods during which no plasma discharge occurs; and at least one gas conduit configured to direct a flow of gas into a region of the pair of electrodes such that the flow of gas includes both longitudinal and rotational components of motion relative to an axis through the pair of electrodes.

In some embodiments is a plasma reactor for converting at least one chemical species to one or more reaction products, the plasma reactor comprising: a reaction chamber; a pair of electrodes in the reaction chamber; a power supply electrically connected to the pair of electrodes; at least one processor configured to control the power supply to cause periodic plasma discharge vents between the pair of electrodes in response to a time-varying voltage applied across the pair of electrodes, wherein the periodic plasma discharge events are separated in time by dwell time periods during which no plasma discharge occurs; and at least one gas conduit configured to direct a flow of gas into a region of the pair of electrodes such that the flow of gas includes both longitudinal and rotational components of motion relative to an axis through the pair of electrodes.

In some embodiments, the reactor further comprising at least one valve associated with the gas conduit, for regulating gas flow volume.

In some embodiments, the at least one processor is configured to control the at least one valve to cause a gas flow with a longitudinal flow velocity of between 0.1 liters per minute and 50 liters per minute.

In some embodiments, the rotational component of motion is sufficient to displace a molecule in the gas flow by a distance greater than or equal to an average diameter of plasma filaments generated during the periodic plasma discharge events.

In some embodiments, the rotational component of motion of the gas flow causes plasma filaments generated during the periodic plasma discharge events to follow a spline-shaped path.

In some embodiments, the dwell time periods are at least ten times longer than discharge times associated with the periodic plasma discharge events.

In some embodiments, the dwell time periods are at least 100 times longer than discharge times associated with the periodic plasma discharge events.

In some embodiments, the periodic plasma discharge events occur at a frequency of at least 50 kHz.

In some embodiments, the periodic plasma discharge events occur at a frequency of at least 100 kHz.

Exemplary Subsequent Filament Follows New Path

In some embodiments, as a result of a longer OFF time than ON time, each new plasma filament may follow a path different from the preceding filament. This feature may help ensure that each generated filament is exposed to more unreacted reactants than quenched reaction products, which can increase reactor efficiency.

In some embodiments is a plasma reactor for converting at least one chemical species to one or more reaction products, the plasma reactor comprising: a reaction chamber; a pair of electrodes in the reaction chamber; and a power supply configured to cause a time-varying voltage across the pair of electrodes, wherein the time-varying voltage is configured to enable generation of a plasma filament between the pair of electrodes during each of a plurality of discharge intervals, such that each of the plurality of discharge intervals is separated in time from another of the plurality of discharge intervals by a dwell interval during which no plasma filament is present between the pair of electrodes, and a duration of the dwell interval is sufficient to cause a subsequent plasma filament generated during a subsequent discharge interval to follow a path different from a path followed by a prior plasma filament generated during a prior discharge interval.

In some embodiments is a plasma reactor for converting at least one chemical species to one or more reaction products, the plasma reactor comprising: a reaction chamber; a pair of electrodes in the reaction chamber; a power supply; at least one processor configured to: control the power supply to cause a time-varying voltage across the pair of electrodes, wherein the time-varying voltage is configured to enable generation of a plasma filament between the pair of electrodes during each of a plurality of discharge intervals, control the power supply such that each of the plurality of discharge intervals is separated in time from another of the plurality of discharge intervals by a dwell interval during which no plasma filament is present between the pair of electrodes, and control the power supply such that a duration of the dwell interval is sufficient to cause a subsequent plasma filament generated during a subsequent discharge interval to follow a path different from a path followed by a prior plasma filament generated during a prior discharge interval.

In some embodiments, an average dwell interval is at least ten times longer than an average discharge interval.

In some embodiments, an average dwell interval is at least 50 times longer than an average discharge interval.

In some embodiments, an average dwell interval is at least 100 times longer than an average discharge interval.

In some embodiments, an average discharge interval is between 50 nanoseconds and 150 nanoseconds in duration, and wherein an average dwell interval is at least 2500 nanoseconds in duration.

In some embodiments, an average dwell interval is at least 10,000 nanoseconds in duration.

In some embodiments, an average dwell interval is at least 15,000 nanoseconds in duration.

In some embodiments, the discharge intervals occur at a frequency of at least 50 kHz.

In some embodiments, the discharge intervals occur at a frequency of at least 100 kHz.

Exemplary Gas Flow Monitoring and Remedial Action

In some embodiments, the gas flow rate may be a parameter important to multiple aspects of the disclosed reactors. Thus, a control system for monitoring the gas flow rate and for taking one or more remedial actions if the flow rate is outside of a predetermined range may be important to the operation and performance of the reactor.

In some embodiments, a control system for a plasma reactor is configured to periodically ignite and extinguish plasma filaments in conjunction with gas flow through the plasma reactor, the control system comprising: at least one processor configured to: receive an indication of gas flow rate through the plasma reactor; determine whether the received indication of gas flow rate indicates a current gas flow rate below a threshold sufficient to enable periodic extinguishing of the plasma filaments; and initiate at least one remedial action if the current gas flow rate is determined to be below the threshold.

In some embodiments, the remedial action includes issuing a warning.

In some embodiments, the warning includes at least one of an audible warning or a visual warning.

In some embodiments, the remedial action includes causing an increase in gas flow within the plasma reactor.

In some embodiments, the remedial action includes increasing an operating speed of at least one pump.

In some embodiments, the remedial action includes causing the plasma reactor to shut down.

Exemplary Parallel Path Reactor

In some embodiments, a plasma reactor having multiple parallel gas flow paths with at least one pair of electrodes disposed within each flow path may offer significantly higher stability than single-flow-path reactors. Such reactors, for example, may be less susceptible to adverse effects caused by gas flow variations.

In some embodiments is a plasma reactor for converting at least one chemical species to one or more reaction products, the plasma reactor comprising: a reactor having a reactor flow path therethrough; a first gas flow chamber in the flow path, the first gas flow chamber defining a first sub-flow path within the reactor flow path; a first pair of electrodes disposed within the first gas flow chamber; at least a second gas flow chamber in the reactor flow path, the second gas flow chamber defining a second sub-flow path within the reactor flow path, wherein the first sub-flow path and the second sub flow path are substantially parallel; at least a second pair of electrodes disposed within the at least a second gas flow chamber; and at least one power supply configured to cause at least one time-varying voltage across each the first pair of electrodes and the second pair of electrodes, to enable sequential generation and termination of plasma filaments within each of the first gas flow chamber and the at least a second gas flow chamber.

In some embodiments is a plasma reactor for converting at least one chemical species to one or more reaction products, the plasma reactor comprising: a reactor having a reactor flow path therethrough; a first gas flow chamber in the flow path, the first gas flow chamber defining a first sub-flow path within the reactor flow path; a first pair of electrodes disposed within the first gas flow chamber; at least a second gas flow chamber in the reactor flow path, the second gas flow chamber defining a second sub-flow path within the reactor flow path, wherein the first sub-flow path and the second sub flow path are substantially parallel; at least a second pair of electrodes disposed within the at least a second gas flow chamber; at least one power supply; and at least one processor configured to cause at least one time-varying voltage across each the first pair of electrodes and the second pair of electrodes, to enable sequential generation and termination of plasma filaments within each of the first gas flow chamber and the at least a second gas flow chamber.

In some embodiments, at least one of the first pair of electrodes or the second pair of electrodes are oriented relative to their respective gas flow chamber such that a field axis between the first pair or electrodes or the second pair of electrodes is arranged parallel to a flow path of the respective gas flow chamber.

In some embodiments, at least one of the first pair of electrodes or the second pair of electrodes are oriented relative to their respective gas flow chamber such that a field axis between the first pair or electrodes or the second pair of electrodes is arranged at a nonzero angle relative to a flow path of the respective gas flow chamber.

In some embodiments, at least one of the first pair of electrodes or the second pair of electrodes are oriented relative to their respective gas flow chamber such that a field axis between the first pair or electrodes or the second pair of electrodes is arranged at an angle of about 90 degrees relative to a flow path of the respective gas flow chamber.

In some embodiments, the plasma reactor includes at least three gas flow chambers whose longitudinal axes are substantially parallel and lie on vertices of a triangle.

In some embodiments, the plasma reactor includes a plurality of gas flow chambers in a hexagonal close-packed arrangement and whose longitudinal axes are substantially parallel to one another.

Exemplary $CO_2$ Dissociator

In some embodiments, a potentially important use case for the disclosed plasma reactors may include the dissociation of carbon dioxide, a well-known industrial pollutant and greenhouse gas. Not only can the disclosed reactor be used to reduce carbon dioxide emissions from various sources, but the system may offer efficiencies of less than 4 eV/mol, which are not possible with current techniques.

In some embodiments is a plasma reactor for dissociating carbon dioxide into carbon monoxide and oxygen, the plasma reactor comprising: a carbon dioxide reaction chamber defining a gas flow path therethrough; an inlet in the reaction chamber, the inlet being configured to supply the gas flow path with carbon dioxide; a pair of electrodes disposed within the gas flow path; a power supply configured to cause a voltage across the pair of electrodes, to enable generation of plasma filaments between the pair of electrodes, wherein the power supply is also configured to control the voltage delivered across the pair of electrodes to vary over time to cause the plasma filaments to repeatedly form and extinguish between the electrodes, in an a manner such that when the plasma filaments are present between the pair of electrodes, the plasma filaments interact with the carbon dioxide, and a disassociation of the carbon dioxide into carbon monoxide and oxygen is enabled to occur; and at least one outlet in the reaction chamber configured to evacuate the carbon monoxide and oxygen from the reaction chamber.

In some embodiments is a plasma reactor for dissociating carbon dioxide into carbon monoxide and oxygen, the plasma reactor comprising: a carbon dioxide reaction chamber defining a gas flow path therethrough; an inlet in the reaction chamber, the inlet being configured to supply the gas flow path with carbon dioxide; a pair of electrodes disposed within the gas flow path; a power supply; at least one processor configured to: cause a voltage across the pair of electrodes, to enable generation of plasma filaments between the pair of electrodes; control the voltage delivered across the pair of electrodes to vary over time to cause the plasma filaments to repeatedly form and extinguish between the electrodes, in an a manner such that when the plasma filaments are present between the pair of electrodes, the plasma filaments interact with the carbon dioxide, and a disassociation of the carbon dioxide into carbon monoxide and oxygen is enabled to occur; and at least one outlet in the reaction chamber configured to evacuate the carbon monoxide and oxygen from the reaction chamber.

In some embodiments, the at least one processor is configured to control filament formation and filament extinguishment such that periods where no filaments are present between the pair of electrodes are longer than periods during which filaments are present between the pair of electrodes.

In some embodiments, the at least one processor is further configured to cause sequential filament discharge intervals to be separated in time by interleaving dwell intervals during which no plasma filament is present between the pair of electrodes, and wherein an average length of the interleaving dwell intervals is at least ten times longer than an average duration of the plurality of discharge intervals.

In some embodiments, the at least one processor is configured to control the supply of carbon dioxide to have a longitudinal flow velocity of between 0.1 liters per minute and 50 liters per minute.

In some embodiments, the reactor further includes at least one gas flow control element configured to impart a rotational component of motion to the supply of carbon dioxide, wherein the rotational component of motion is sufficient to displace a carbon dioxide molecule in the supply of carbon dioxide by a distance greater than or equal to an average diameter of plasma filaments generated during the plurality of plasma discharge intervals.

In some embodiments, the average length of the interleaving dwell intervals is at least 50 times longer than the average duration of filament formation intervals.

In some embodiments, the average length of the interleaving dwell intervals is at least 100 times longer than the average duration of the plurality filament formation intervals.

In some embodiments, generation of the plasma filaments occurs at a rate of at least 50 kHz.

In some embodiments, generation of the plasma filaments occurs at a rate of at least 100 kHz.

Exemplary Recycling of Surplus Energy to Reduce $CO_2$ Emissions

In some embodiments, a plasma generator may be installed at the outlets of industrial plants to use surplus energy from the industrial plant to power a plasma generator that breaks down $CO_2$.

In some embodiments is a system for using surplus energy in an industrial process to reduce carbon dioxide emission generated by the industrial process, the system comprising: a plasma generator connectable to the source of surplus energy, the plasma generator including a pair of electrodes electrically connected to a power supply; an inlet for associating the plasma generator with a carbon dioxide outlet of the industrial process, to enable carbon dioxide emissions from the industrial process to flow into a region of the pair of electrodes; and a power supply configured to provide energy to the plasma generator in order to cause a sequence of plasma filaments to be formed, punctuated by an extinguishing of each filament before another filament is formed, to thereby convert the carbon dioxide in a region of the pair of electrodes to dissociate into carbon and oxygen.

In some embodiments is a system for using surplus energy in an industrial process to reduce carbon dioxide emission generated by the industrial process, the system comprising: a plasma generator connectable to the source of surplus energy, the plasma generator including a pair of electrodes electrically connected to a power supply; an inlet for associating the plasma generator with a carbon dioxide outlet of the industrial process, to enable carbon dioxide emissions from the industrial process to flow into a region of the pair of electrodes; and at least one processor for controlling a supply of energy to the plasma generator in order to cause a sequence of plasma filaments to be formed, punctuated by an extinguishing of each filament before another filament is formed, to thereby convert the carbon dioxide in a region of the pair of electrodes to dissociate into carbon and oxygen.

In some embodiments, a time between a first filament extinguishing and a next, second filament forming is at least 50 times greater than a time during which a the first or the second filaments persist.

Exemplary Plasma Generated $XeF_2$

In some embodiments, a potentially important use case for the disclosed plasma reactor is xenon fluoride generation through a plasma-assisted combination of methane and xenon.

In some embodiments, a plasma reactor for generating xenon fluoride, the plasma reactor comprising: a xenon fluoride reaction chamber defining a gas flow path therethrough; at least one inlet in the reaction chamber, the at least one inlet being configured to supply the gas flow path with a supply of a fluorocarbon gas and xenon gas; a pair of electrodes disposed within the gas flow path; a power supply configured to: cause a time-varying voltage across the pair of electrodes, wherein the time-varying voltage is configured to enable generation of a plasma filament between the pair of electrodes; and control the voltage delivered across the pair of electrodes in a time-varying manner to cause the plasma filaments to repeatedly form and extinguish between the electrodes, in an a manner such that when the plasma filaments are present between the pair of electrodes, the plasma filaments interact with the xenon gas and the fluorocarbon gas, and the interaction causes formation of xenon fluoride; and at least one outlet in the reaction chamber configured to evacuate the xenon fluoride from the reaction chamber.

In some embodiments, a plasma reactor for generating xenon fluoride, the plasma reactor comprising: a xenon fluoride reaction chamber defining a gas flow path therethrough; at least one inlet in the reaction chamber, the at least one inlet being configured to supply the gas flow path with a supply of a fluorocarbon gas and xenon gas; a pair of electrodes disposed within the gas flow path; a power supply; at least one processor configured to: cause a time-varying voltage across the pair of electrodes, wherein the time-varying voltage is configured to enable generation of a plasma filament between the pair of electrodes; control the voltage delivered across the pair of electrodes in a time-varying manner to cause the plasma filaments to repeatedly form and extinguish between the electrodes, in an a manner such that when the plasma filaments are present between the pair of electrodes, the plasma filaments interact with the xenon gas and the fluorocarbon gas, and the interaction causes formation of xenon fluoride; and at least one outlet in the reaction chamber configured to evacuate the xenon fluoride from the reaction chamber.

In some embodiments, the generated xenon fluoride includes $XeF_2$.

In some embodiments, the supply of fluorocarbon gas includes $CF_4$ (tetrafluorocarbon).

In some embodiments, the at least one processor is further configured to control flow of a gas mixture including the supply of xenon gas and the supply of fluorocarbon gas with a longitudinal flow velocity along the gas flow path of between 0.1 liters per minute and 50 liters per minute.

In some embodiments, the reactor further includes at least one gas flow control element configured to impart a rotational component of motion to a gas mixture including the supply of xenon gas and the supply of fluorocarbon gas, wherein the rotational component of motion is sufficient to displace a molecule in the gas mixture by a distance greater than or equal to an average diameter of plasma filaments generated during the plurality of plasma discharge intervals.

In some embodiments, the at least one processor is further configured to cause sequential filament formation intervals to be separated in time by interleaving dwell intervals during which no plasma filament is present between the pair of electrodes, and wherein an average length of the interleaving dwell intervals is at least ten times longer than an average duration of the plurality of filament formation intervals.

In some embodiments, the average length of the interleaving dwell intervals is at least 50 times longer than the average duration of the plurality of discharge intervals.

In some embodiments, the average length of the interleaving dwell intervals is at least 100 times longer than the average duration of the plurality of discharge intervals.

In some embodiments, generation of the plasma filaments occurs at a rate of at least 50 kHz.

In some embodiments, generation of the plasma filaments occurs at a rate of at least 100 kHz.

Exemplary Plasma Generated Syn as

In some embodiments, a further potentially important use case for the disclosed plasma reactor is syn gas generation, using about half as much energy as current microwave systems.

In some embodiments, a plasma reactor for generating syn gas, the plasma reactor comprising: a syn gas reaction chamber defining a gas flow path therethrough; at least one inlet in the reaction chamber, the at least one inlet being configured to supply the gas flow path with a supply of a first gas containing carbon and oxygen and a second gas containing hydrogen; a pair of electrodes disposed within the gas flow path; a power supply configured to cause a voltage across the pair of electrodes and alter the voltage across the electrodes in a time-varying manner to cause plasma filaments to repeatedly form and extinguish between the electrodes, in a manner such that when the plasma filaments are present between the pair of electrodes, the plasma filaments interact with the first gas and the second gas, and the interaction causes formation of syn gas; and at least one outlet in the reaction chamber configured to evacuate the syn gas from the reaction chamber.

In some embodiments, a plasma reactor for generating syn gas, the plasma reactor comprising: a syn gas reaction chamber defining a gas flow path therethrough; at least one inlet in the reaction chamber, the at least one inlet being configured to supply the gas flow path with a supply of a first gas containing carbon and oxygen and a second gas containing hydrogen; a pair of electrodes disposed within the gas flow path; a power supply; at least one processor configured to cause a voltage across the pair of electrodes and alter the voltage across the electrodes in a time-varying manner to cause plasma filaments to repeatedly form and extinguish between the electrodes, in a manner such that when the plasma filaments are present between the pair of electrodes, the plasma filaments interact with the first gas and the second gas, and the interaction causes formation of syn gas; and at least one outlet in the reaction chamber configured to evacuate the syn gas from the reaction chamber.

In some embodiments, the first gas includes CO2.

In some embodiments, the second gas includes $CH_4$.

In some embodiments, the syn gas includes a mixture of carbon monoxide and hydrogen.

In some embodiments, the mixture of the first gas and the second gas has a longitudinal flow velocity along the gas flow path of between 0.1 liters per minute and 50 liters per minute.

In some embodiments, the at least one processor is further configured to cause sequential filament formation intervals to be separated in time by interleaving dwell intervals during which no plasma filament is present between the pair of electrodes, and wherein an average length of the interleaving dwell intervals is at least ten times longer than an average duration of the plurality of filament formation intervals.

In some embodiments, reactor further including at least one gas flow control element configured to impart a rotational component of motion to a gas mixture including the first gas and the second gas, wherein the rotational component of motion is sufficient to displace a molecule in the gas mixture by a distance greater than or equal to an average diameter of plasma filaments generated during the plurality of plasma discharge intervals.

In some embodiments, the average length of the interleaving dwell intervals is at least 50 times longer than the average duration of the plurality of filament formation intervals.

In some embodiments, the average length of the interleaving dwell intervals is at least 100 times longer than the average duration of the plurality of filament formation intervals.

In some embodiments, generation of the plasma filaments occurs at a rate of at least 50 kHz.

In some embodiments, generation of the plasma filaments occurs at a rate of at least 100 kHz.

The following description provides several additional examples consistent with the presently disclosed embodiments.

Example 1

An exemplary process for converting $CO_2$ to CO and oxygen such as by $CO_2 \rightarrow CO + \frac{1}{2}O_2$ using pulse plasma-chemical reactor was demonstrated. Initial $CO_2$ was injected to a plasma reactor having two electrodes (anode and cathode) inserted coaxially to a quartz cylinder. Both electrodes had a shape demonstrated in FIG. 17 (11). Each electrode was made as a copper cylinder with tungsten rods. In both electrodes, gas flow goes through the central hole in copper part.

Power supply outputs was connected with electrodes. The output capacitor was 300 pF. By this way, repetitive hot plasma filament creation and extinguishing was obtained. Lifetime of plasma filament was about 300 ns. Repetition frequency was 60 kHz. Desirable gas velocity in reactor was reached by using a recycling gas pump.

Parameters of the experiment were as follows:
Input $CO_2$ flow rate: 1.2 $m^3/h$
Output power supply power: 900 W
Recycling pump flow rate: 30 $m^3/h$
Quartz chamber internal diameter: 40 mm
Product gases concentration were as follows:
CO: 15%
$O_2$: 7.5%

Example 2

An exemplary process for conversion of $CO_2$ to CO and oxygen in a reaction such as $CO_2 \rightarrow CO + \frac{1}{2}O_2$ using pulse plasma-chemical reactor was demonstrated. Initial $CO_2$ was injected to plasma reactor having two electrodes (anode and cathode) inserted coaxially to a quartz cylinder. Both electrodes had a shape as demonstrated in FIG. 17 (10). Each electrode was made from copper. In both electrodes gas flow went through central hole in copper part. Power supply outputs were connected with electrodes. The output capacitor was 300 pF. By this way, repetitive hot plasma filament creation and extinguishing was obtained. The lifetime of the plasma filament was about 300 ns. The repetition frequency was 60 kHz.

Desirable gas velocity in reactor was reached by using a recycling gas pump.

Parameters of the experiment were as follows:
Input $CO_2$ flow rate: 1.2 $m^3/h$
Output power supply power: 1200 W
Recycling pump flow rate: 30 $m^3/h$
Quartz chamber internal diameter: 40 mm
Product gases concentration were as follows:
CO: 13%
$O_2$: 6.5%

Example 3

Process of conversion of the $CO_2$ to CO and oxygen in the reaction $CO_2 > CO + \frac{1}{2}O_2$ using pulse plasma-chemical reactor was demonstrated. Initial $CO_2$ was injected to a plasma reactor having two electrodes (anode and cathode) inserted coaxially to a quartz cylinder. The cathode electrode had a shape as demonstrated in FIG. 17 (10). The cathode was made from copper. The anode had a shape as demonstrated in FIG. 17 (11). The anode was made as a copper cylinder with tungsten rods. In both electrodes gas flow goes through central hole in the copper part. Power supply outputs was connected with electrodes. The output capacitor was 300 pF. By this way repetitive hot plasma filament creation and extinguishing was obtained. The lifetime of plasma filament was about 300 ns. The repetition frequency was 60 kHz. Desirable gas velocity in the reactor was reached by using of recycling gas pump.

Parameters of the experiment:
Input $CO_2$ flow rate: 1.2 $m^3/h$
Output power supply power: 950 W
Recycling pump flow rate: 30 $m^3/h$
Quartz chamber internal diameter: 40 mm
Product gases concentration:
CO: 14%
$O_2$: 7%

Example 4

A process for conversion of the $CO_2$ to CO and oxygen in the reaction $CO_2 > CO + \frac{1}{2}O_2$ using pulse plasma-chemical reactor was demonstrated. Initial $CO_2$ was injected to a plasma reactor having two electrodes (anode and cathode) inserted coaxially to a quartz cylinder. Both electrodes had a shape as demonstrated in FIG. 17 (11). Each electrode was made as a copper cylinder with tungsten rods. In both electrodes, gas flow goes through a central hole in the copper part. A power supply output was connected with electrodes. The output capacitor was 300 pF. By this way, repetitive hot plasma filament creation and extinguishing was obtained. The lifetime of the plasma filament was about 300 ns. The repetition frequency was 60 kHz. Desirable gas velocity in reactor was reached by using a recycling gas pump.

Parameters of the experiment:
Input $CO_2$ flow rate: 1.2 $m^3/h$
Output power supply power: 930 W
Recycling pump flow rate: 20 $m^3/h$
Quartz chamber internal diameter: 40 mm
Product gases concentration:
CO: 15%
$O_2$: 7.5%

Example 5

A process for conversion of the $CO_2$ up to CO and oxygen in reaction $CO_2 > CO + \frac{1}{2}O_2$ using a pulse plasma-chemical reactor was demonstrated. Initial $CO_2$ was injected to a plasma reactor having two electrodes (anode and cathode) inserted coaxially to a quartz cylinder. Both electrodes had a shape as demonstrated in FIG. 17 (11). Each electrode was made as a copper cylinder with tungsten rods. In both electrodes, gas flow goes through a central hole in the copper part. Power supply outputs were connected with electrodes. The output capacitor was 300 pF. By this way, a repetitive hot plasma filament creation and extinguishing was obtained. The lifetime of the plasma filament was about 300 ns. The repetition frequency was 60 kHz. Desirable gas velocity in reactor was reached by using a recycling gas pump.

Parameters of the experiment:
Input $CO_2$ flow rate: 1.2 $m^3/h$
Output power supply power: 1000 W
Recycling pump flow rate: 15 $m^3/h$
Quartz chamber internal diameter: 40 mm
Product gases concentration:
CO: 14%
$O_2$: 7.0%

Example 6

A process of conversion of the $CO_2$ up to CO and oxygen in reaction $CO_2 \rightarrow CO + \frac{1}{2}O_2$ using a pulse plasma-chemical reactor was demonstrated. Initial $CO_2$ was injected to a plasma reactor having two electrodes (anode and cathode) inserted coaxially to a quartz cylinder. Both electrodes had a shape as demonstrated in FIG. 17 (11). Each electrode was made as a copper cylinder with tungsten rods. In both electrodes, gas flow goes through a central hole in copper part. Power supply outputs were connected with electrodes. The output capacitor was 300 pF. By this way, repetitive hot plasma filament creation and extinguishing was obtained. The lifetime of the plasma filament was about 300 ns. The repetition frequency was 60 kHz. Desirable gas velocity in reactor was reached by using a recycling gas pump.

Parameters of the experiment:
Input $CO_2$ flow rate: 1.2 $m^3/h$
Output power supply power: 900 W
Recycling pump flow rate: 30 $m^3/h$
Quartz chamber internal diameter 40 mm
Product gases concentration:
CO: 15%
$O_2$: 7.5%

Example 7

A process of conversion of the 50% $CO_2$ and 50% of $CH_4$ mixture to syngas (CO and $H_2$ mixture) in the reaction $CO_2 + CH_4 \rightarrow 2CO + 2H_2$ using pulse plasma-chemical reactor. Initial $CO_2$ was injected to the plasma reactor having two electrodes (anode and cathode) inserted coaxially to a quartz cylinder. Both electrodes had a shape as demonstrated in FIG. 17 (11). Each electrode was made as a copper cylinder with tungsten rods. In both electrodes, gas flow goes through a central hole in the copper part. Power supply outputs were connected with electrodes. The output capacitor was 300 pF. By this way, repetitive hot plasma filament creation and extinguishing was obtained. The lifetime of the plasma filament was about 200 ns. The repetition frequency was 60 kHz. Desirable gas velocity in the reactor was reached by using a recycling gas pump.

Parameters of the experiment:
Input $CO_2$ flow rate: 1.2 $m^3/h$
Input $CH_4$ flow rate: 1.2 $m^3/h$
Output power supply power: 1300 W
Recycling pump flow rate: 30 $m^3/h$
Quartz chamber internal diameter 40 mm
Product gases concentration:
CO: 15%
$H_2$: 15%

Example 8

A process for conversion of a 50% $CO_2$ and 50% $CH_4$ mixture to syngas (CO and $H_2$ mixture) in the reaction $CO_2 + CH_4 \rightarrow 2CO + 2H_2$ using pulse a plasma-chemical reactor was demonstrated. Initial $CO_2$ was injected to a plasma reactor having two electrodes (anode and cathode) inserted coaxially to a quartz cylinder. Both electrodes had a shape as demonstrated in FIG. 17 (11). Each electrode was made as a copper cylinder with tungsten rods. In both electrodes, gas flow goes through a central hole in copper part. Power supply outputs were connected with electrodes. The output capacitor was 300 pF. By this way, repetitive hot plasma filament creation and extinguishing was obtained. The lifetime of the plasma filament was about 200 ns. The repetition frequency was 60 kHz. Desirable gas velocity in reactor was reached by using a recycling gas pump.

Parameters of the experiment:
Input $CO_2$ flow rate: 1.2 $m^3/h$
Input $CH_4$ flow rate: 1.2 $m^3/h$
Output power supply power: 1100 W
Recycling pump flow rate: 20 $m^3/h$
Quartz chamber internal diameter: 40 mm
Product gases concentration:
CO: 15%
$H_2$: 15%

Example 9

A process for conversion of a 50% $CO_2$ and 50% of $CH_4$ mixture to syngas (CO and $H_2$ mixture) in the reaction $CO_2 + CH_4 \rightarrow 2CO + 2H_2$ using pulse plasma-chemical reactor was demonstrated. Initial $CO_2$ was injected to a plasma reactor having two electrodes (anode and cathode) inserted coaxially to a quartz cylinder. Both electrodes had a shape as demonstrated in FIG. 17 (11). Each electrode was made as a copper cylinder with tungsten rods. In both electrodes, gas flow goes through a central hole in the copper part. Power supply outputs were connected with electrodes. The output capacitor was 300 pF. By this way, repetitive hot plasma filament creation and extinguishing was obtained. The lifetime of plasma filament was about 200 ns. The repetition frequency was 60 kHz. Desirable gas velocity in reactor was reached by using a recycling gas pump.

Parameters of the experiment:

Input $CO_2$ flow rate: 1.2 $m^3$/h

Input $CH_4$ flow rate: 1.2 $m^3$/h

Output power supply power: 900 W

Recycling pump flow rate: 10 $m^3$/h

Quartz chamber internal diameter 40 mm

Product gases concentration:

CO: 15%

$H_2$: 15%

Example 10

A process for conversion of a 50% $CO_2$ and 50% $CH_4$ mixture to syngas (CO and $H_2$ mixture) in the reaction $CO_2+CH_4 \rightarrow 2CO+2H_2$ using pulse plasma-chemical reactor was demonstrated. Initial $CO_2$ was injected to a plasma reactor having two electrodes (anode and cathode) inserted coaxially to a quartz cylinder. Both electrodes had a shape as demonstrated in FIG. 17 (11). Each electrode was made as a copper cylinder with tungsten rods. In both electrodes, gas flow goes through additional tangential holes to create rotating flow. The central hole was closed.

Power supply outputs were connected with electrodes. The output capacitor was 300 pF. By this way, repetitive hot plasma filament creation and extinguishing was obtained. The lifetime of plasma filament was about 200 ns. The repetition frequency was 60 kHz. Desirable gas velocity in reactor was reached by using a recycling gas pump.

Parameters of the experiment:

Input $CO_2$ flow rate: 1.2 $m^3$/h

Input $CH_4$ flow rate: 1.2 $m^3$/h

Output power supply power: 1100 W

Recycling pump flow rate: 30 $m^3$/h

Quartz chamber internal diameter: 40 mm

Product gases concentration:

CO: 15%

$H_2$: 15%

Example 11

A process for conversion of a 50% $CO_2$ and 50% of $CH_4$ mixture to syngas (CO and $H_2$ mixture) in the reaction $CO_2+CH_4 \rightarrow 2CO+2H_2$ using pulse plasma-chemical reactor was demonstrated. Initial $CO_2$ was injected to a plasma reactor having two electrodes (anode and cathode) inserted coaxially to a quartz cylinder. Both electrodes had a shape as demonstrated on FIG. 17 (11). Each electrode was made as a copper cylinder with tungsten rods. In both electrodes, gas flow goes through additional tangential holes to create rotating flow. The central hole was closed. Power supply outputs were connected with electrodes. The output capacitor was 300 pF. By this way, repetitive hot plasma filament creation and extinguishing was obtained. The lifetime of plasma the filament was about 200 ns. The repetition frequency was 60 kHz. Desirable gas velocity in reactor was reached by using a recycling gas pump.

Parameters of the experiment:

Input $CO_2$ flow rate: 1.2 $m^3$/h

Input $CH_4$ flow rate: 1.2 $m^3$/h

Output power supply power: 900 W

Recycling pump flow rate: 20 $m^3$/h

Quartz chamber internal diameter: 40 mm

Product gases concentration:

CO: 15%

$H_2$: 15%

Examples of reactor configurations and operational parameters (along with exemplary results obtained during experiments) are provided in the sections below.

Example 12

Production of acetylene from a 70/30 mixture of methane/hydrogen at atmospheric pressure was demonstrated.

The gas flow rate (in the recycling line) was 20 m/hour. The cathode had tungsten pins with variable length decreasing in direction of tangential flow. The anode has 6 tangential holes with diameter 6 mm each. The breakdown frequency was 52 kHz. The gap between cathode and anode pins was 40 mm. The calculated tangential velocity of gas in electrodes zone was 30 m/s which is more than $f*5*10^{-4}=25$ m/s.

Power supply based on IGBT bridge schematic and high voltage transformer which was loaded on one pair of half-wave rectifiers having a high voltage diode and capacitor wherein one rectifier of the pair charges the positive electrode positively and another rectifier charges the negative electrode negatively and, serially to rectifiers, was installed an inductor and capacitor (FIG. 12).

During the experiment, a rotation of plasma position was obtained, and stable breakdown voltage was inside 9-10 kV region. The efficiency of energy transfer from power supply to plasma was 82%. The plasma energy cost of acetylene molecule production was 8 eV per molecule.

Example 13

Production of acetylene from a 70/30 mixture of methane/hydrogen at atmospheric pressure was demonstrated.

The gas flow rate (in the recycling line) was 10 m/hour. The cathode had tungsten pins with variable length decreasing in direction of tangential flow. The anode had 6 tangential holes with diameter 6 mm each. The breakdown frequency was 52 kHz. The gap between cathode and anode pins was 40 mm. The calculated tangential velocity of gas in the electrode zone was 15 m/s which is less than $f*5*10^{-4}=25$ m/s.

The power supply was based on a IGBT bridge schematic and a high voltage transformer was loaded on one pair of half-wave rectifiers having a high voltage diode and capacitor wherein one rectifier of the pair charges the positive electrode positively and another rectifier charges the negative electrode negatively and, serially to rectifiers, was installed an inductor and capacitor (FIG. 12).

During the experiment, a rotation of plasma position was not obtained, and attaching of plasma filament to electrodes pins was detected. The breakdown voltage was inside 6-10 kV region. The efficiency of energy transfer from the power supply to the plasma was 65%. The plasma energy cost of acetylene molecule production was 8.5 eV per molecule.

Example 14

Dissociation of $CO_2$ at atmospheric pressure was demonstrated. The gas flow rate (in the recycling line) was 20 m/hour. The cathode had tungsten pins with variable length decreasing in direction of tangential flow. The anode had 6 tangential holes with diameter 6 mm each. The breakdowns frequency was 52 kHz. The gap between cathode and anode pins was 40 mm. The calculated tangential velocity of gas in electrodes zone was 30 m/s which is more than $f*5*10^{-4}=25$ m/s.

The power supply was based on a IGBT semi-bridge schematic and high voltage transformer with primary winding with midpoint. The transformer was loaded on one pair of half-wave rectifiers having a high voltage diode and capacitor wherein one rectifier of the pair charges the positive electrode positively and another rectifier charges the negative electrode negatively and, serially to the rectifiers, was installed an inductor and capacitor (FIG. 12).

During the experiment, a rotation of plasma position was obtained, and attaching of plasma filament to electrodes pins was not detected. The breakdown voltage was inside 8-9 kV region. The efficiency of energy transfer from the power supply to the plasma was 80%. The plasma energy cost of CO production was 4.2 eV per molecule.

Example 15

Dissociation of $CO_2$ at atmospheric pressure was demonstrated. The discharge chamber had four channels (FIG. 10). The gas flow rate (in the recycling line) was 20 m/hour. The cathode had tungsten pins of variable length decreasing in direction of tangential flow. The anode had 6 tangential holes with diameter 6 mm each. The breakdown frequency was 12 kHz. The gap between cathode and anode pins was 40 mm. The calculated tangential velocity of gas in electrodes zone was 8 m/s which is more than $f*5*10^{-4}=6$ m/s.

Figure 13:
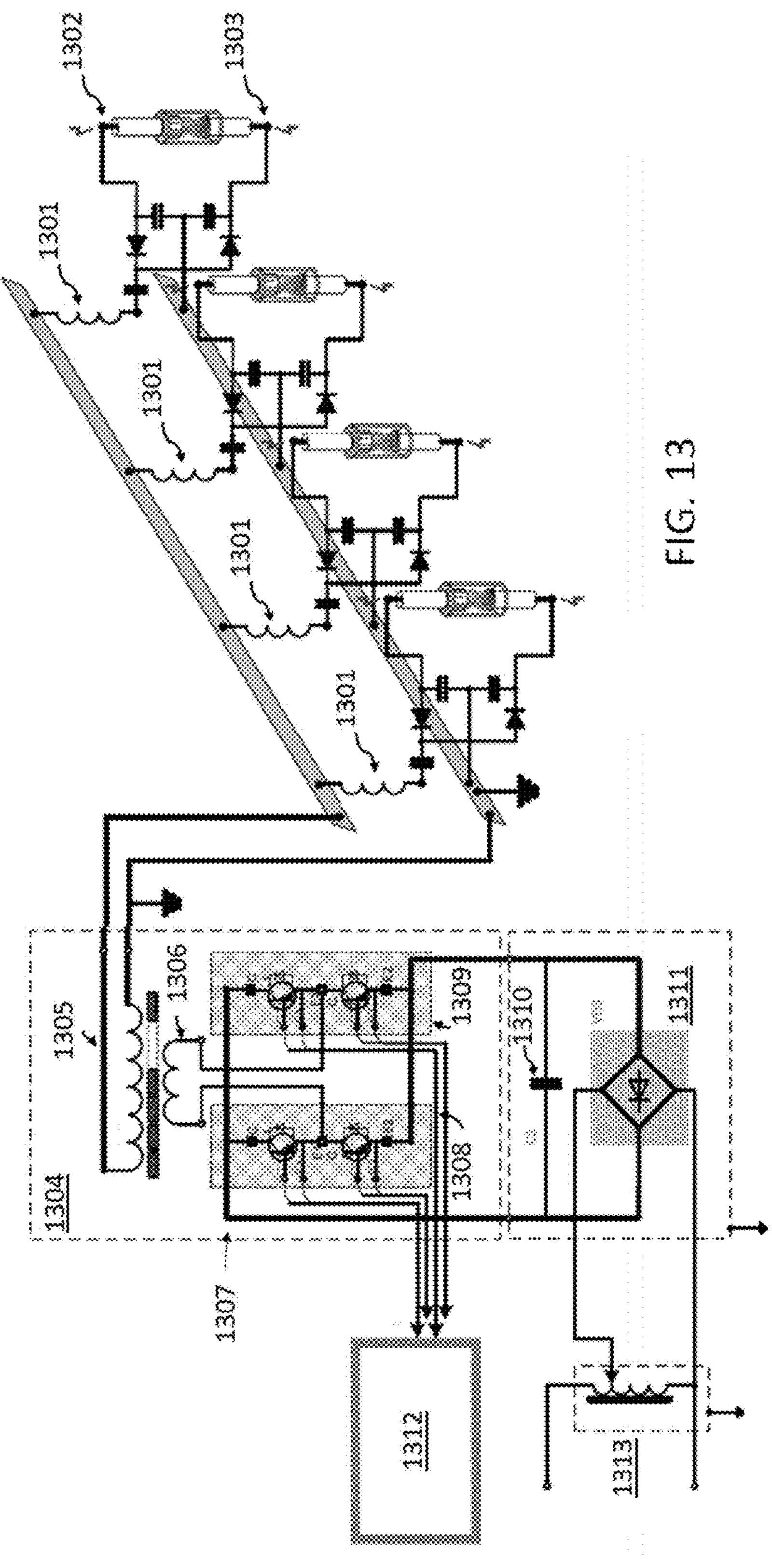
FIG. 13 shows a schematic representation of a plasma reactor with four channels of nanosecond hot plasma pulse electric discharge, according to exemplary disclosed embodiments.

The power supply was based on a IGBT semi-bridge schematic and high voltage transformer with primary winding with midpoint. The transformer was loaded on one four pairs of half-wave rectifiers having a high voltage diode and capacitor wherein one rectifier of the pair charges the positive electrode positively and another rectifier charges the negative electrode negatively and, serially with each pair of rectifiers, was installed an inductor and capacitor (FIG. 13). In FIG. 13, 1301 depicts inductors (5.5 mHn), 1302 depicts a point of −30 kV, 1303 depicts a point of +30 kV, 1304 depicts a power module, 1305 depicts a secondary winding (220 turns), 1306 depicts a primary winding (3 turns), 1307 depicts a point of +500V, 1308 depicts a IGBT module (CM200DU—24NFH), 1309 depicts a IGBT module (CM200DU—24NFH), 1310 depicts a capacitor (6×820 uF, 200V), 1311 depicts a diode bridge (4×60EPF12), 1312 depicts a driver, 1313 depicts a variac (110V, 20 A).

During the experiment, a rotation of plasma position was obtained, and attaching of plasma filament to electrodes pins was not detected. The breakdown voltage was inside 8-9 kV region. The efficiency of energy transfer from the power supply to the plasma was 81%. The plasma energy cost of CO production was 4.1 eV per molecule.

Example 16

Dissociation of $NH_4$ at atmospheric pressure was demonstrated. The gas flow rate (in the recycling line) was 20 m/hour. The cathode had tungsten pins with variable length decreasing in direction of tangential flow. The anode had 6 tangential holes with diameter 6 mm each. The breakdown frequency was 52 kHz. The gap between cathode and anode pins was 40 mm. The calculated tangential velocity of gas in electrodes zone was 30 m/s which is more than f*5*10-4=25 m/s.

The power supply was based on a IGBT semi-bridge schematic and high voltage transformer with primary winding with midpoint. The transformer was loaded on one pair of half-wave rectifiers consisting from high voltage diode and capacitor wherein one rectifier of the pair charges the positive electrode positively and another rectifier charges the negative electrode negatively and, serially to rectifiers, was installed an inductor and capacitor (FIG. 12).

During the experiment, a rotation of plasma position was obtained, and attaching of plasma filament to electrodes pins was not detected. The breakdown voltage was inside 9-10 kV region. The efficiency of energy transfer from the power supply to the plasma was 80%. The plasma energy cost of $NH_4$ dissociation was 3.5 eV per molecule.

What is claimed is:

1. A plasmachemical reactor with nanosecond pulse electric discharge generation, wherein the reactor comprises:

one or more cylindrical channels having a gas input system and output system;

a high voltage positive electrode and a high voltage negative electrode in each channel; and a gas swirling system in each channel for increasing local tangential gas velocity at electrodes ends; wherein the pulse electric discharge generation has a frequency f, the tangential gas velocity is greater than $f*5*10^{-3}$ m/s, and wherein each high voltage positive electrode and each high voltage negative electrode has a cylindrical shape and at least one electrode has a tangential channel in the electrode body and a circular row of equal length rods on a flat end and at least one electrode having no tangential channel has a circular row of rods having lengths which decrease along a direction of gas rotation.

2. The plasmachemical reactor of claim 1, wherein the gas swirling system has an auger shaped electrode isolator, a tangential channel in one or more electrode, and a tangential channel in the gas input and/or the gas output systems.

3. The plasmachemical reactor of claim 1, wherein a power supply provides an alternating voltage supply to the positive electrode and the negative electrode of each N channels by N pairs of half-wave rectifiers having a high voltage diode and a capacitor wherein one rectifier of each pair charges the positive electrode positively and another rectifier charges the negative electrode negatively.

4. The plasmachemical reactor of claim 3, wherein a high voltage inductor and/or high voltage capacitor is connected in series to the diode of each half-wave rectifier.

5. The plasmachemical reactor of claim 3, wherein the power supply includes a half-wave fly-back.

6. The plasmachemical reactor of claim 4, wherein the power supply includes a full-wave push-pull circuit with an insulated gate bipolar transistor (IGBT) semi-bridge.

7. The plasmachemical reactor of claim 4, wherein the power supply is a full-wave push-pull circuit with IGBT semi-bridge with midpoint transformer primary winding.

8. The plasmachemical reactor of claim 4, wherein the power supply a full-wave push-pull with IGBT bridge.

* * * * *